United States Patent [19]
Jernigan

[11] 3,984,156
[45] Oct. 5, 1976

[54] OBJECTIVE PLOTTING OF VISUAL FIELDS BY EYE MOVEMENT MONITORING

[75] Inventor: Marvin E. Jernigan, Weston, Mass.

[73] Assignee: Narco Scientific Industries, Inc., Fort Washington, Pa.

[22] Filed: Sept. 12, 1974

[21] Appl. No.: 505,339

[52] U.S. Cl. .................................. 351/6; 351/39
[51] Int. Cl.² .......................................... A61B 3/10
[58] Field of Search ............... 351/6, 17, 23, 24, 39, 351/7

[56] References Cited
UNITED STATES PATENTS

| | | |
|---|---|---|
| 3,172,404 | 3/1965 | Copenhaver et al. ............. 351/24 X |
| 3,473,868 | 10/1969 | Young et al. ....................... 351/7 X |
| 3,718,386 | 2/1973 | Lynn et al. ......................... 351/23 X |
| 3,827,789 | 8/1974 | Molner et al. ......................... 351/23 |
| 3,864,030 | 2/1975 | Cornsweet ....................... 351/39 X |

Primary Examiner—Paul A. Sacher
Attorney, Agent, or Firm—Wolf, Greenfield & Sacks

[57] ABSTRACT

An apparatus for measuring and evaluating a subject's visual field presents a target image, consisting of a spot of light, at a series of selected locations within the subject's visual field. Means are provided to monitor his resulting eye movement and positions in response to each target presentation. A projection apparatus presents the target images at various locations and in a programmed sequence. The apparatus also includes means for making a photographic plot of those presented targets which the subject has seen or missed, as desired. Determination of whether subject has seen or missed a particular target is evaluated by logic systems which discriminate between eye movement and positions displaying characteristics indicative of whether the subject has seen or missed the target. The logic discriminates between blinks, hunting eye movements and other characteristic positions and movements which are indicative of the subject having seen the target. Means also are provided to enable selective coarse or fine mapping of selected regions of the subject's visual field.

22 Claims, 23 Drawing Figures

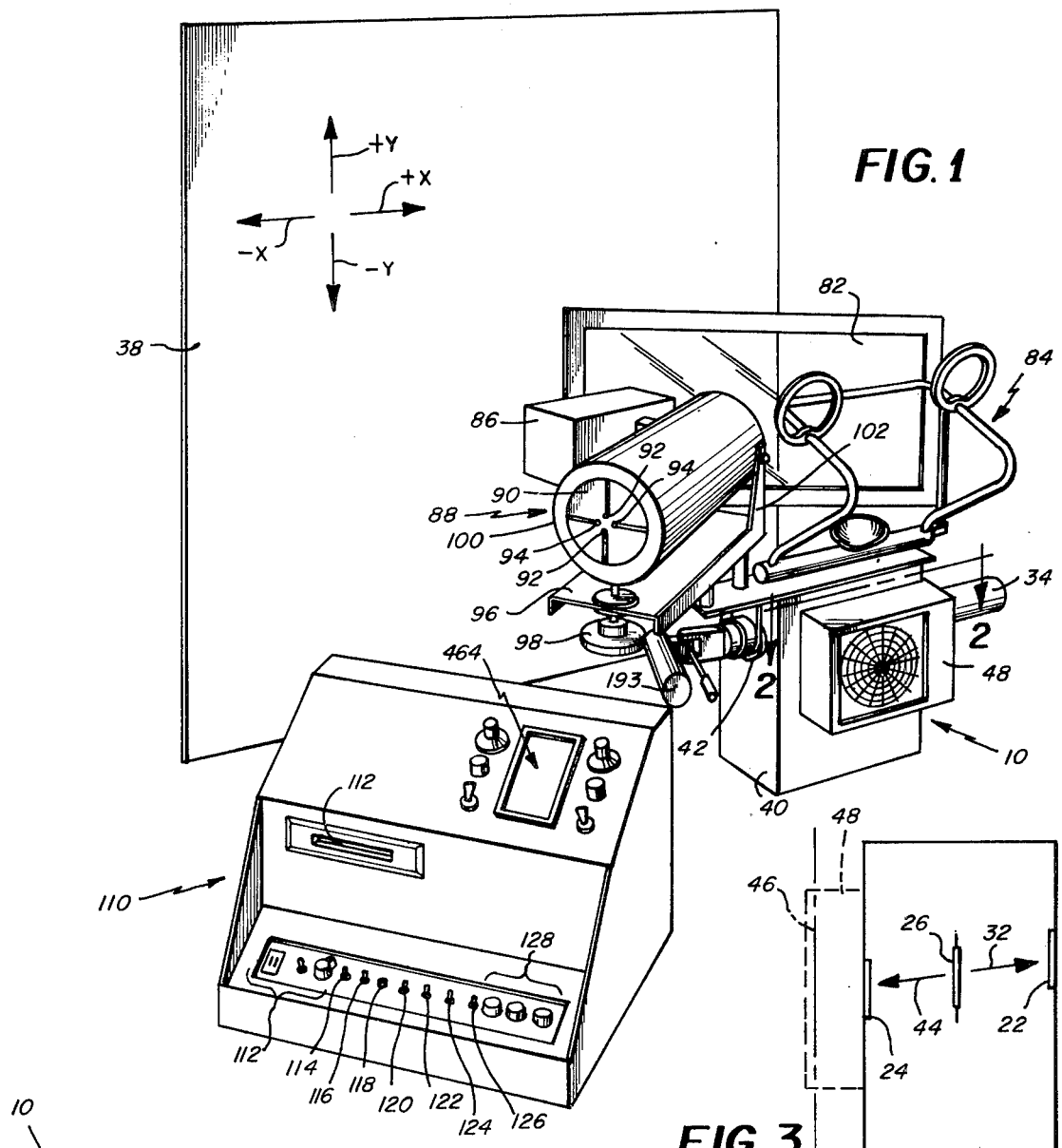
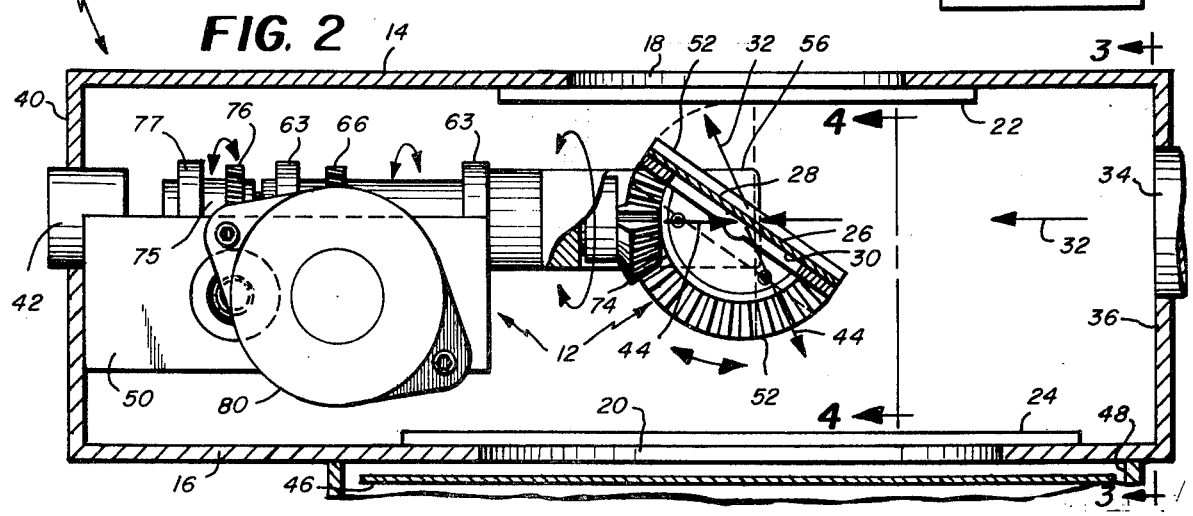

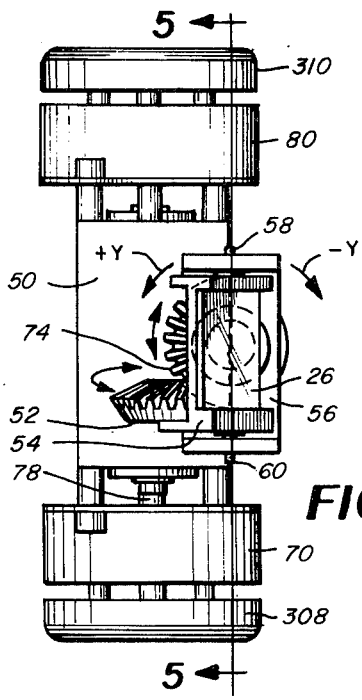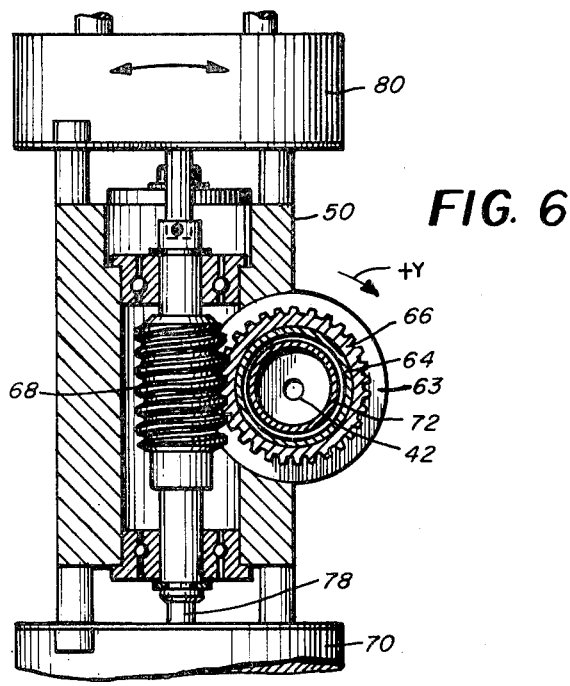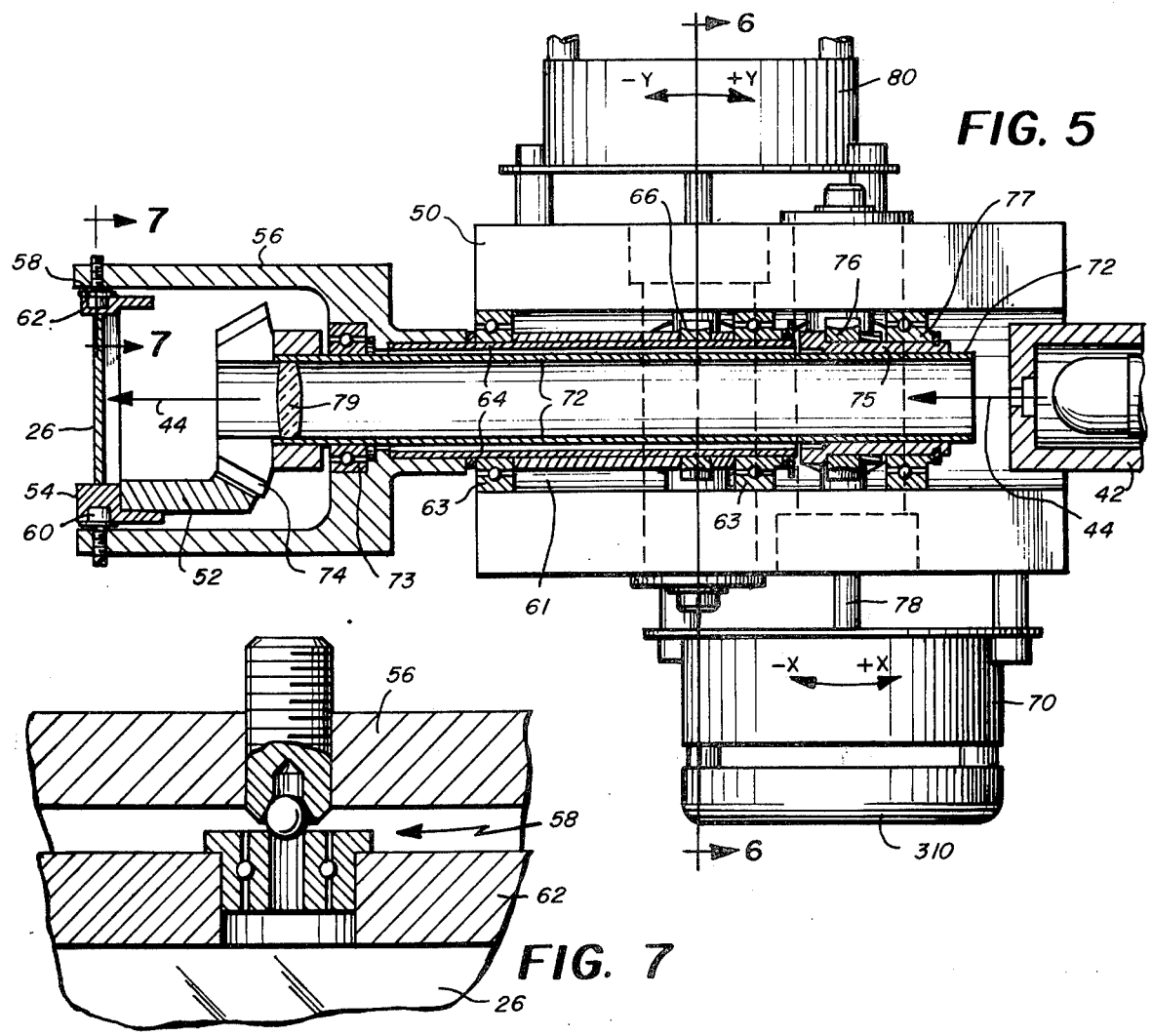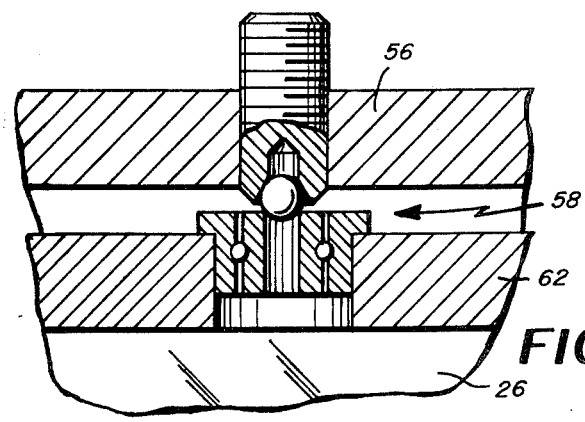

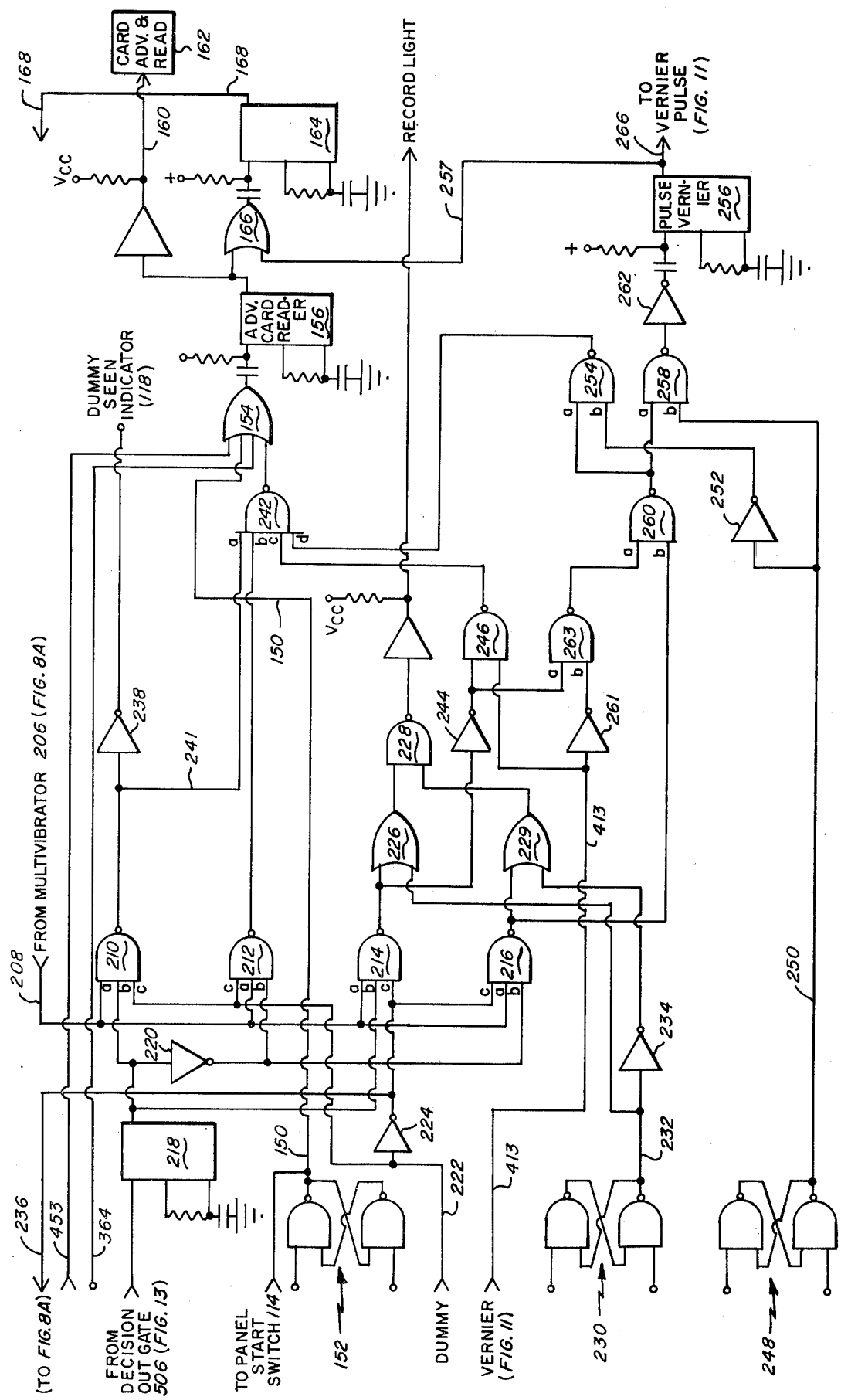

FIG. 9
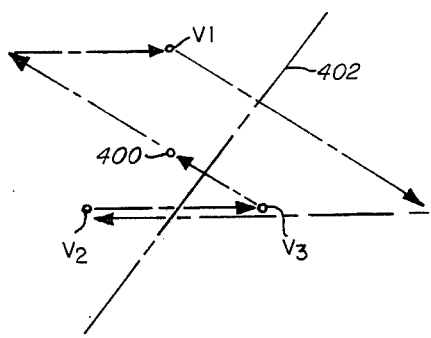
FIG. 9A
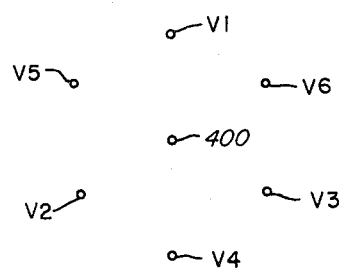

FIG. 12H

OBJECTIVE PLOTTING OF VISUAL FIELDS BY EYE MOVEMENT MONITORING

BACKGROUND OF THE INVENTION

Measurement of one's visual field is important for a variety of reasons including the diagnosis of glaucoma as well as other human visual system diseases or impairments. In general, the prior techniques for determining one's visual field and any blind spots have been quite slow and tedious and require a definite subjective response from the person being tested in order to determine whether he has sighted the target at a particular location in his visual field. Additionally, the previously employed tests require administration by one having relatively high degree of skill such as an ophthalmic technician, optometrist or ophthalomologist. For example, in the most common type of visual field test, a hand held target such as a small disc at the end of a wand, is moved about the subject's visual field by the examiner while the subject fixates on a central point. During movement of the hand held target through the subject's field, the examiner asks the subject repeatedly whether he can see the movable target as it is passing from location to location. The examiner may plot, manually, the location of each point which is seen by the subject, or alternatively, he may plot those locations which the subject is unable to see, and which, therefore, define his blind spot.

In order to overcome the uncertainties and difficulties in the foregoing testing techniques some attempts have been made to automate partly the foregoing visual field test, such as employing an arrangement for automatically presenting a series of targets to the subject. Although these devices are somewhat faster than the completely manual test described above, they still are relatively slow and require that the subject respond consciously and intentionally when he sees the target. For example, the response may be verbal or may be indicated by the subjective manipulation of a lever or a button.

Also among the primary difficulties in obtaining fast and accurate plots of the subject's visual field is that the examiner must be assured that the subject's line of sight is directed toward a central fixation point or other known reference point before the target is presented to him. In some instances this may be quite difficult when problems of communication exist between the subject and the examiner as, for example, when testing the young, the aged, or persons whose native language is different than that of the examiner. Furthermore, any such difficulties render efficient and accurate testing still more complicated because it may confuse the results of the test.

A further difficulty in conducting visual field tests with prior techniques is that an indication by the subject that he has seen the target may be the result of hunting eye movements in which, he did not at first actually see the target but moved his eyes about slightly, in a searching motion, and then having seen the target, then moved his eyes directly to it. The present invention employs means for discriminating between such hunting movements and movements in which the presented target was initially seen by the subject.

It is among the primary objects of the invention to provide an apparatus for determining a subject's visual field which avoids the foregoing and other difficulties.

SUMMARY OF THE INVENTION

The invention takes advantage of the natural voluntary or involuntary eye movements which results when a target is presented suddenly to a subject within his visual field. Measurement of the eye movement or change in eye position in response to presentation of the target is employed to determine whether the subject has seen the target. The eye movements may be detected and monitored by a technique described in U.S. Pat. No. 3,473,868 in which the direction and magnitude of the eye movements are translated into electrical signals. Electronic logic means are provided for discriminating between signals which represent eye movements characteristic of the subject having actually seen the target from other types of eye movements such as blinks, hunting or searching movements or the like which produce electrical impulses unrelated to the subject's actual initial detection of the target image. The logic means includes a decision logic circuit which evaluates whether the subject actually visually detected the target by reference to the number and magnitude of the subject's eye movements within an extended time interval which includes the interval during which the target image is presented and a short period thereafter.

The invention employs a target image projector which develops a narrow collimated light beam and directs the beam sequentially toward selected locations on a screen which is within the subject's expected visual field. The position of the intermittent light beam and target image on the screen is determined by reflecting the beam, from its source, off one surface of a double faced mirror toward the screen. The attitude of the mirror is controllable to selectively direct the beam in the desired direction by stepping motors which are positioned in accordance with preprogrammed digital information. The location of the target image on the screen, as presented to the subject, may be recorded permanently and automatically on photographic film incorporated into the projector. In the preferred embodiment, the photographic film is of the Polaroid type which enables immediate inspection after the test has been completed. The photographic recording is made by employing a second light beam which is reflected off the opposite face of the controlled mirror toward the photographic film. The second, reflected beam is directed along the same axis as the first projection beam, but from the opposite direction and impinges on the film at a location which is dependent on the angle of incidence of the beam to the mirror which corresponds to the direction of the light beam which impinges on the target screen. Shutters are provided in association with each of the first and second light beams, the first shutter being employed to control the timing and duration of presentation of the target light and the second shutter means being employed to expose the photographic film to the second beam. In another mode of operation only those points which are not observed are photographically recorded to provide a plot of the subject's blind spot or spots. The second shutter is controlled automatically in response to the logic circuitry which evaluates whether the subject has seen or missed a particular target.

The stepping motor arrangement for changing the attitude of the mirror also enables the device to be programmed to present a sequence of targets on the screen in close proximity to each other rather than more widely spaced locations about the screen. This enables more precise plotting and evaluation of an area of the subject's blind spot or spots after the more coarse presentation of the target spots has indicated the general location of the blind spot or spots. The device may be operated in a mode in which the more precise evaluation is effected automatically when a subject has missed a presented target.

It is among the primary objects of the invention to provide an improved technique for determining and plotting a subject's visual field.

Another object of the invention is to provide an improved technique in which the subject's response to a series of targets presented at various locations in his visual field is determined objectively without subjective response on his part.

A further object of the invention is to provide an arrangement for making a permanent record of the subject's visual field.

Still another object of the invention is to provide an improved technique for plotting and measuring a subject's visual field without requiring that the test be administered by highly skilled personnel.

Another object of the invention is to provide an improved technique by which eye movements characteristic of a subject's actual sighting of a target presented within his visual field may be discriminated from other types of eye movements automatically.

DESCRIPTION OF THE DRAWINGS

The foregoing and other objects and advantages of the invention will be understood more fully from the following further description thereof, with reference to the accompanying drawings wherein:

FIG. 1 is an illustration of the invention set up in readiness for use;

FIG. 2 is a sectional plan illustration of the mirror positioning mechanism as seen from line 2—2 of FIG. 1 and showing portions of the mechanism broken away;

FIG. 3 is a sectional elevation as seen along the line 3—3 of FIG. 2;

FIG. 4 is a side elevation of the mirror positioning mechanism as seen along the line 4—4 of FIG. 2;

FIG. 5 is a sectional view of the mirror positioning mechanism as seen along the line 5—5 of FIG. 4;

FIG. 6 is a sectional elevation of the mirror positioning mechanism as seen along the line 6—6 of FIG. 5;

FIG. 7 is an enlarged illustration of the low friction bearing by which the mirror is mounted;

FIG. 8A and 8B illustrate a schematic of the control logic electronics of the invention;

FIG. 9 is an illustration of the relative locations of the vernier target images with respect to each other and to the location of the primary target image on the presentation screen;

FIG. 9A is an illustration of an alternative configuration of vernier target locations;

FIG. 12H is a DC plot representative of a blink;

DESCRIPTION OF THE PREFERRED EMBODIMENT

Figure 8A:
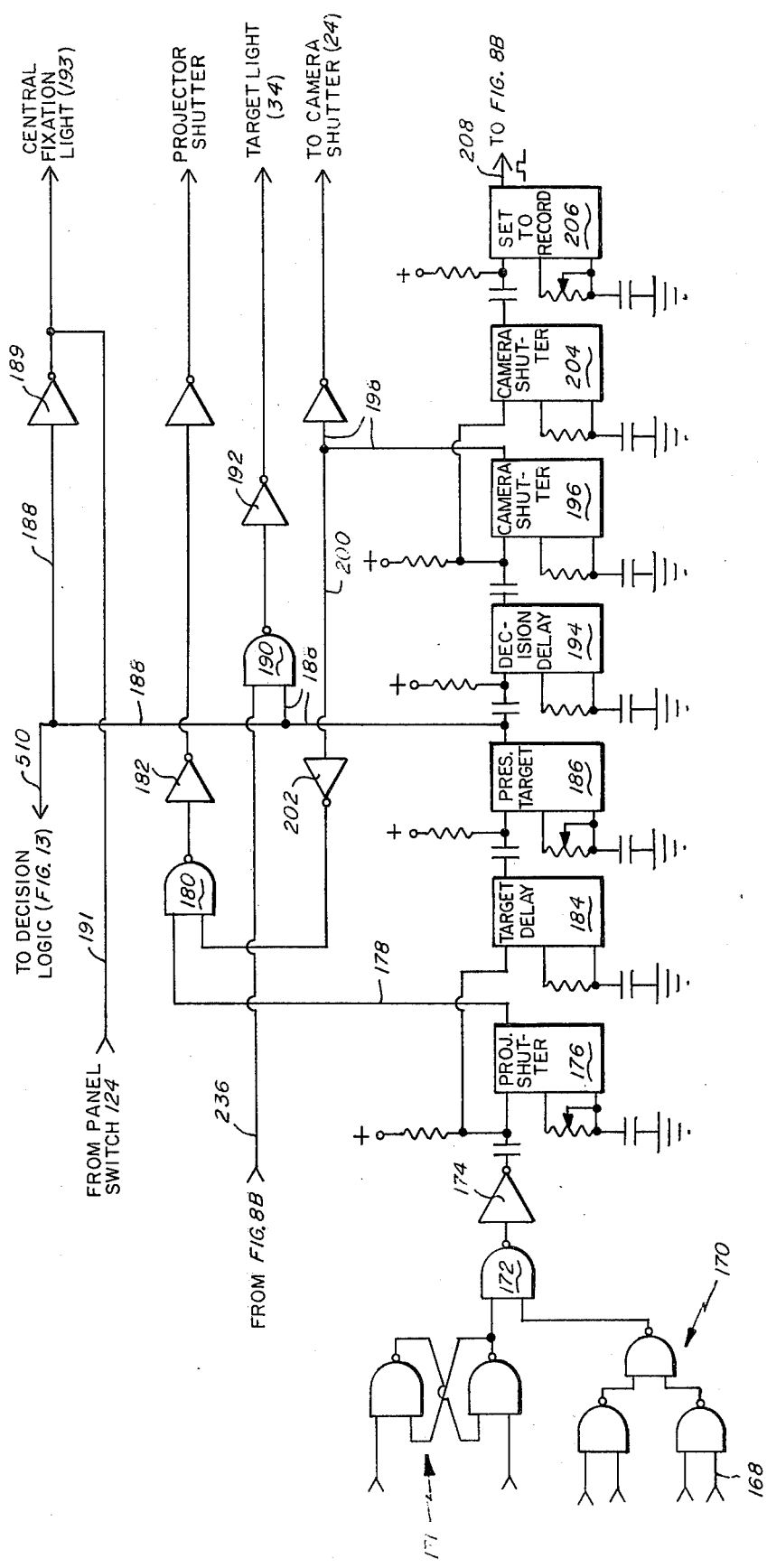

FIGS. 1–3 shows generally the apparatus employed in the invention which includes a projector-camera housing 10 in which is mounted the mirror mechanism 12. The housing 10 includes a front wall 14 and a rear wall 16, having apertures 18, 20 respectively which can be opened or closed by a projection shutter 22 and film shutter 24. The mirror mechanism 12 includes a double faced mirror 26 having a front face 28 and a rear face 30. The mirror 26 is arranged so that it will reflect the light beam 32 from a projection light 34, mounted to a sidewall 36 of the housing, 10 through the projection shutter 22 and onto the projection screen 38. The opposite sidewall 40 of the housing 10 supports a second light source 42 which directs a beam of light 44 toward the rear face 30 of the mirror 26 along the same axis as that of the light beam from the projection light 34. The beam from the second light source 42 is reflected from the mirror surface 30 in a direction which is opposite that of the reflected projection beam 32 from the front face 28 of the mirror 26. The recording light beam 44 is directed toward a film plane, indicated diagrammatically at 46 and disposed at the rear of the housing 10 by any of a variety of well-known film holding devices 48. The double faced mirror 26 thus directs the projection beam 32 to a selected location on the screen and simultaneously directs the recording beam 44 (when it is operated) to a corresponding location in the film plane 46, as controlled by the attitude of the mirror 26.

The mirror 26 is mounted for adjustable movement by the mirror mechanism 12. The mirror mechanism is mounted to a support block 50 which is secured to the interior of the housing 10. As shown more fully in FIGS. 2–7, the mirror mechanism 12 includes a driven bevel gear segment 52. The mirror 26 is secured to and across the diameter of gear 52 by a bracket 54 and lies in a plane perpendicular to that of the gear 52. The mirror 26 and gear 52 are supported for rotation in unison about the central axis of the gear 52 by means of a yoke 56 having a low friction bearing 58 which supports the upper edge of the mirror, by bracket 62, and a low friction bearing 60 which supports the opposite face of the gear 52, by bracket 54, to enable the mirror 26 and gear 52 to rotate in unison about a common axis defined by the bearings 58, 60. The yoke 56 is mounted for rotation about a horizontal axis to rotate the mirror 26 and gear 52 bodily about that horizontal axis. To this end the yoke 56 is secured to the end of an outer cylinder 64 which is mounted for rotation to the block 50 by bearings 63. The cylinder 64 has a gear 66 secured thereto which is rotated by a worm gear 68 which is driven, in turn, by a stepping motor 80 mounted to the block 50. The mirror 26 and gear 52 are rotatable with respect to the yoke 56 by means of an inner cylinder 72 which extends through and is rotatable within the outer cylinder 64. One end of the inner cylinder 72 extends into and is supported at the yoke by bearing 73 and has a bevel gear 74 secured thereto which meshes with driven bevel gear 52. The opposite end of the inner cylinder 72 extends outwardly beyond the end of the outer cylinder 64 and has a collar 75 secured thereto. The collar 75, in turn, is rotatably mounted to the block 50 by bearing 77. The inner cylinder 64 is driven by a gear 76 secured thereto which is driven by the worm gear as described above. The worm gear is secured to shaft 78 of stepping motor 70. The stepping motors 70, 80 of the mirror mechanism 12 are operated by the position logic system which, in turn, is controlled by the digital information on the program card or the vernier positioning system to orient the mirror 26 to present the target image at any desired location within the subject's visual field and also direct the recording light beam (when operated) to a corresponding location in the film plane. The second light source 42 is mounted to a sidewall of the housing in alignment with the axis of rotation of the inner and outer cylinders 72, 64. The inner cylinder 72 is hollow along its length to enable the light beam from the second light source to impinge on and be reflected by the mirror 26.

For convenience in the further description herein, the mirror axis of rotation extending through the bearings 58, 60 will be referred to as the X axis and the axis of rotation of the mirror by means of the yoke 56 will be considered as the Y axis. Similarly, step motor 70 will be referred to as the X step motor and step motor 80 will be referred to as the Y step motor.

In order to monitor the position and eye movements of the subject during the test, the device may include a partially reflective plate 82 mounted above and forwardly of the housing 10 so as to be directly in front of the subject's view when his head is properly placed in the head rest and chin support 84. Plate 82 is adapted to enable the subject to view the screen 38 and is disposed at an angle to his general line of sight to enable a light source 86, preferably infrared, to reflect from the plate 82 and illuminate the subject's eyes. The image from the subject's eyes is, in turn, reflected from the plate 82 toward an imaging arrangement 88 which includes a ground glass screen 90 on which the reflected image of the subject's eye may be focused, employing the technique described in the aforementioned U.S. patent. As described in that patent a pair of vertically spaced photoelectric cells 92 and horizontally spaced photoelectric cells 94 are located on or adjacent the screen 90 and are aligned with selected regions of the image of the subject's eye on the screen 90. Variations in the output signals from the photocells 92, 94 are dependent on the direction and magnitude of the subject's eye movements and their signals are processed in the logic circuitry as described more fully herein. Imaging arrangement 88 preferably is mounted for adjustment to the housing 10 to facilitate initial alignment of the photocells 92, 94 with the subject's eye image on the screen 90. This may include a bracket 96 pivoted for horizontal movement to the housing 10 and a vertical elevation screw 98 carried by the bracket 96 and in engagement with the end of the barrel 100, the other end of the barrel 100 being pivoted to the bracket at trunnions 102.

GENERAL DESCRIPTION OF OPERATION

Figure 14:
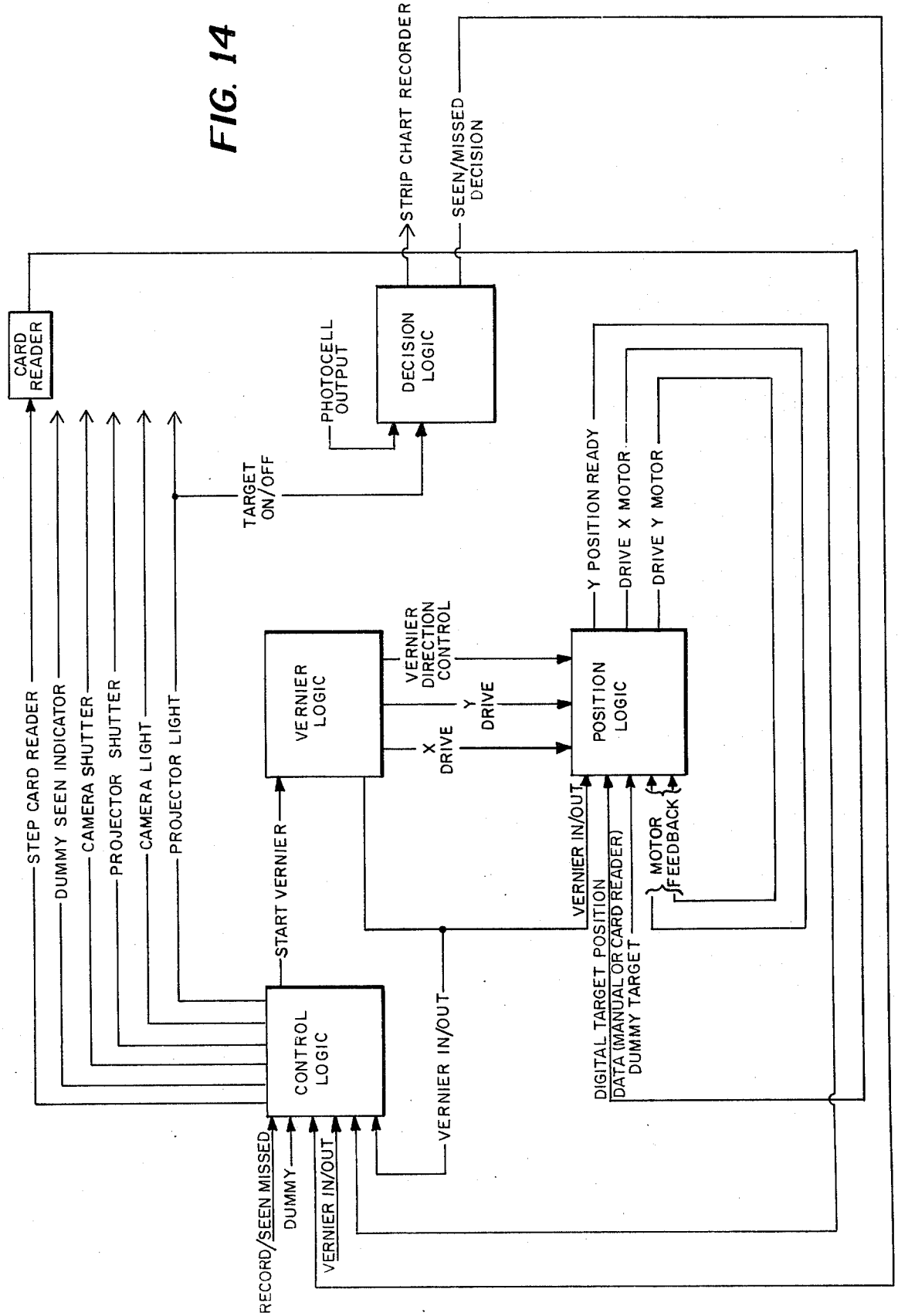
FIG. 14 is a block diagram illustrating diagrammatically the relationship between the various functions of the logic circuits.

The invention employs a number of electronic logic systems which are interrelated as shown diagrammatically in FIG. 14. The primary logic systems include a control logic circuit, a positioning logic circuit, a decision logic circuit and a vernier logic circuit. A typical cycle might begin by an output from the control logic circuit to step a card reader and read the card bearing digital information corresponding to an intended location of the target image. The digital information is fed into the position logic circuitry which controls the mirror positioning mechanism 12 and positions the mirror in the intended attitude. In the embodiment of the invention described, digital data is included in the card for the positions of each of the X and Y motors with the Y motor being positioned first and then the X motor. When the Y motor has been driven to its intended position, a "Y position ready" signal is fed into the control logic to cause the card reader to advance to the next column of X positioning information on the digital information card. This is fed into the position logic and the X motor is driven to its intended position. During the stepping of the motors 70, 80 the position of the X or Y step motor being driven is fed back to the position logic circuit for comparison with the intended position corresponding to the digital positioning input. The control logic includes means for delaying operation of the other elements of the invention during positioning of the mirror. After that delay has elapsed and the mirror has been positioned the control logic resumes operation to open the projector shutter and turn on the projector light to present the target image on the projection screen while simultaneously turning off the central, reference fixation target light. The target image will be located at a predetermined angular distance, within approximately 40°, from the central reference fixation target. The position and movement of the subject's eyes, during and slightly after presentation of the target image, is monitored by the photocells 92, 94 and their output is fed into the decision logic which evaluates whether the subject has seen or missed the presented target. The seen/missed decision from the decision logic is fed back into the control logic and, depending on whether the manual inputs to the control logic were set to record seen or missed targets, the control logic will operate the camera shutter and the camera light to make, or not to make, a photographic plot of that target image.

Means are also incorporated in the invention for checking the subject's cooperation in the test by enabling "dummy" targets (those in which there is no target presented) to be "presented" to the subject. In the event that the output from the photocells indicates eye movement indicating that the subject did "see" the dummy target, the control logic causes a "dummy seen" indicator light on the operator's control panel to turn on thus advising the operator of the subject's uncooperativeness.

It should be noted that the shutter mechanisms are opened and closed whether a real target or a dummy target is presented. This is desirable when the shutter mechanism selected makes audible operating sounds which might be heard by the subject. By operating the shutters for each mode the subject cannot tell audibly whether the target is real or a dummy.

The invention also includes means for evaluating the subject's visual field closely about the region in which he missed an actually presented target. For this purpose the vernier logic circuit may be employed. The vernier logic circuit is set into operation when the control logic receives a signal from the decision logic indicating that the subject missed an actual target. When the vernier logic circuit is initiated, the control logic is disabled from operating the card reading mechanism and the positioning of the mirror, to present the vernier target images, is controlled entirely by the vernier logic circuit. When the vernier target images have been presented the vernier logic causes the position logic to return the mirror to the attitude which it was in before the vernier sequence and the positioning logic is then enabled to be responsive to the digital positioning information from the card reader. The control logic causes the card reader to be advanced to the next informational word corresponding to the next intended target location and the sequence is begun anew.

The electronic logic systems may be housed conveniently in a control module 110 which houses the card advancing and reading mechanism which includes an exposed slot 112 to receive the card. The module 110 may also house a strip chart recorder 464 to provide a supplemental record of subject's eye test. The module 110 also includes a control panel which includes a manual target positioning means 112, a start switch 114, a stop switch 116, a "dummy seen" indicator light 118, a record seen/missed selector switch 120, a vernier in/out switch 122, a manually controllable switch 124 for turning the reference fixation target on or off, a "disable double saccade" switch 126 and a number of intensity controls 128 for the target light, recording light and reference fixation light.

DESCRIPTION OF CONTROL LOGIC

FIGS. 8A and 8B show the circuitry controlling and coordinating the operation of the machine. The sequence of operation is begun by applying a pulse to line 150 through flip-flop 152 and through OR gate 154 to trigger monostable multivibrator 156. When first starting the sequence of operation the starting pulse may be applied to line 150 through manual start switch 114. Succeeding pulses are applied to line 150 through flip-flop 152 which is operated in a manner described herein. The high output pulse from multivibrator 156 is amplified and fed through line 160 to initiate operation of a card advancing and reading device 162 which may be of any of a variety of commercially available designs. It should be noted that while the present embodiment of the invention is described as employing digital programming information in the form of a machine readable card, other information, storage and reading techniques may be employed such as tape or the like as is well known in the art. The pulse from multivibrator 156 is also applied to multivibrator 164 through OR gate 166. Multivibrator 164 has a delay constant (will remain at a high output) sufficient to delay presentation of the target image long enough to enable the card advancing and reading mechanism 162 to position the card so that its digital information may be read as well as to provide sufficient delay for the stepping motors of mirror mechanism 12 to position the mirror, as for example, a delay of approximately 1 second. The output from multivibrator 164 also is directed through line 168 to a gating circuit 170 (FIG. 8A) which has an AND function. The output from gate circuit 170 is fed through NAND gate 172 and inverter 174 to apply a high input to monostable multivibrator 176. The other inputs to the gating circuit 170 are from the positioning logic circuitry, described below, which is effective to apply a high input to gating circuit 170 when the mirror has been positioned in accordance with the digital information on the input card, as described herein. With the mirror properly positioned, monostable multivibrator 176 is triggered and its output is directed, through line 178 to actuate the driving mechanism for the projection shutter 22 to open the projection shutter. In the embodiment shown this may be achieved by applying the output from the multivibrator 176 to the input of an enabled NAND gate 180, inverting the low output from gate 180 to a high state through inverter 182 and applying the high pulse to the shutter mechanism to open the shutter. Multivibrator 176 has a time delay sufficient to maintain the projection shutter open while the target light is being presented. For example, the delay may be of the order of 2.75 seconds.

It is desirable to delay the operation of the target light until the projection shutter 22 has been opened fully. To this end simultaneously with actuation of monostable multivibrator 176, the pulsed output from inverter 174 is also applied to monostable multivibrator 184 which has a delay constant of the order of 55 milliseconds, depending on the time required to open the shutter fully. The high output pulse from multivibrator 184 is fed into monostable multivibrator 186 which, in turn, controls operation of the target light. The output from multivibrator 186 causes the target light 34 to turn on through line 188 to NAND gate 190 and inverter 192 to the switch mechanism (not shown) for the target light. Gate 190 is normally enabled because of the normally high state of line 236 as will be described. Multivibrator 186 has a delay constant sufficient to remain in a high output state and present the target image for a predetermined time interval long enough to afford the subject a sufficient opportunity to detect and respond to the target. By way of example, a delay constant of the order of 2.2 seconds would be typical. It is desirable to switch the central reference fixation target light 193 off when the target image is presented. This may be accomplished automatically by connecting line 188 through an inverter 189 to the central fixation light. When multivibrator 186 switches high to present the target light, the output from inverter 189 switches low to extinguish the central fixation light 193. When multivibrator 186 returns to its stable state, turning off target light 134, the output from inverter 189 will return to its high state to re-present the central reference fixation target. In an alternative mode of operation the central fixation light 193 may be maintained on at all times, including the time in which the target is presented, by line 191 which is connected to the panel switch 124.

The subject's eye movements and positions are monitored during an extended time interval which includes the predetermined time interval of the presentation of the target image. As described, the output from the photocells 92, 94 is evaluated by the decision logic circuitry to determine whether the subject actually visually detected the target image. In order to provide ample opportunity for the decision to perform its function the output from multivibrator 186 is applied concurrently to monostable multivibrator 194 which has a delay constant sufficient for the subject's eye positions and movements to be monitored by the photocells 92, 94 and the resulting signals processed through the decision logic circuitry. The delay constant of multivibrator 194 preferably is somewhat longer than the time constant of multivibrator 186 to enable the decision logic to evaluate eye movements after the target image has been extinguished, for the full extended time interval. The delay may be, for example, of the order of 3 1 seconds. This is desirable because the subject's eyes may move after the target light has been extinguished, as when returning his vision to the central fixation point as described herein.

When the decision logic has evaluated whether a subject actually visually detected the presented target image, it then remains for the photographic recording system to make, or not make, a photographic plot of the target image location, as determined by the mode of operation which the examiner has selected. To this end as multivibrator 194 returns to its stable, low output state, the pulse triggers multivibrator 196, and the output of multivibrator 196 is directed through line 198 to the camera shutter mechanism to open the camera shutter 24. At the same time, the output from multivibrator 196 is directed through line 200 through inverter 202 to apply a low signal at NAND gate 180 which will insure that the projector shutter is closed. This precludes ambient light from reaching the film plane as might occur if the projection shutter 22 remained opened at the same time as the camera shutter. Simultaneously with the actuation of multivibrator 196, the output from multivibrator 194 is applied to monostable multivibrator 204 which is effective to delay further sequencing of the photographic recording functions until the camera shutter 24 is open fully. The delay will depend on the characteristics of the shutter mechanism and may for example, be of the order of 55 milliseconds. It may be noted that monostable multivibrator 196 has a time delay constant sufficient for the logic and control circuits to "decide" whether or not to make a photographic plot of the relative location of the target image as described below. By way of example, the delay may be of the order of 1.2 seconds. When the camera shutter 24 has been opened fully, the return to its stable, low output state of multivibrator 204 triggers multivibrator 206. Multivibrator 206 sets the control logic circuitry in readiness to cause a photographic record of the position of the target to be made, depending on whether the target light was actually presented, whether it was a "dummy" in which case no target would have been presented, whether the subject "saw" or "missed" the target or dummy and whether the intended mode of operation, as controlled by a suitable selector switch on the panel of the control box, is set to record "seen" or "missed" points.

As shown in FIGS. 8A and 8B the output from multivibrator 206 is directed through line 208 to one of the inputs a of each of the NAND gates 210, 212, 214, 216. Each of gates 210, 212, 214 and 216 also has an input b which is controlled by the decision output from the decision logic circuitry. As described more fully herein, the output from the decision logic circuitry is a signal which is indicative of whether the subject's eye positions and movements where characteristic of his having "seen" the target. As shown in FIG. 8B the output from the decision logic circuitry is applied to monostable multivibrator 218 and the output from multivibrator 218 is directly connected to input b of each of NAND gates 210 and 214. The output from multivibrator 218 is also connected, through inverter 220 to input b of each of NAND gates 212 and 216. Each of the gates 210, 212, 214, 216 also includes an input c, as through line 222, which controls gates 210, 212, 214, 216 in the event that a "dummy" target was presented. The state of line 222 may indicate a "dummy" either by a manual dummy presentation switch on the control panel or from appropriate digital information programmed into the card. Line 222 is connected directly to input c of each of the NAND gates 210, 212 and is applied, in an inverted form, through inverter 224 to input c of each of the NAND gates 214, 216.

Gates 210, 212 are effective to detect, respectively, whether a dummy signal was "seen" or whether it was "missed," as it should have been. Gates 214, 216 discriminate between actually presented targets which are "seen" or "missed." For example, assuming that an actually presented target was seen and that the manually controlled panel switch (which controls the output of flip-flop arrangement 230), to selectively record points seen or points missed, is in the "record seen" configuration. Where the target was actually presented, line 222 is at a low state which applies low inputs to terminals c of gates 210 and 212 and high inputs to terminals c of gates 214, 216. Inputs a of each of gates 210, 212, 214, 216 are high at this time, from the output of multivibrator 206 through line 208. A target which was actually seen will result in an output pulse from the decision logic to pulse multivibrator 218. This will result in a high input to terminal b of NAND gate 214 and a low input to terminal b of NAND gate 216. The resulting high output of gate 214 is passed through OR gate 226 and the high output from OR gate 226 is applied to NAND gate 228. The other input to NAND gate 228 is high because of its connection to the output of OR gate 229, which was high because of the high output from NAND gate 216. This results in a pulse at the output from NAND gate 228 which triggers the recording light source. Had the subject under test missed the presented target, input a to NAND gate 216 would have remained in its inverted high state thus maintaining its output low which, through OR gate 229, would maintain NAND gate 228 in its previous state. The result would be no output pulse from NAND gate 228 and the record light source would not be triggered.

If it is desired to record the missed targets, thus providing a photographic plot of only the missed points, the panel controlled record seen/missed selector 230 may be set manually to switch the state at line 232 from high to low which sets one of the input terminals of NAND gate 228 at a high state through inverter 234 and OR gate 229. The low state of line 232 is applied directly to one of the inputs to OR gate 226. When the presented target is missed, there will be no pulse from multivibrator 218 and its output will remain low, resulting in a high output from gate 216 which, through OR gate 226, will generate a low output pulse from NAND gate 228, thus triggering the recording light source and making a photographic plot of that missed point. If, however, the target is seen, the output pulse from multivibrator 218 will be applied to input b of NAND gate 214 which will switch gate 214 to a low output state with a corresponding low output state from OR gate 226. NAND gate 228 will not be triggered and no photographic recording will be made.

In those instances where it is desired to spot check the subject's response by providing a "dummy" target, the state of line 222 may be changed from low to high either by a manually operable switch on the face of the control panel or by preprogrammed digital instruction on the program card. In either event, when the state of line 222 is switched to high, the high state is applied to inputs c of NAND gates 210, 212, respectively. Inputs a of gates 210, 212 are also at a high state. Gates 214, 216 are disabled from operating the recording light during this mode of operation by means of the low output of the inverter 224. The low output from inverter 224 also is applied, through line 236 to an input of NAND gate 190, thus disabling gate 190 (FIG. 8A) and precluding operation of the target light.

When a "dummy target" is presented and "missed" input b to gate 210 will be low, resulting in a high output from gate 210 which, is inverted through inverter 238. The output from inverter 238 is employed to control the operation of an indicator light 240 on the panel which, when lit, indicates that the subject moved his eyes when there was no target presented. Here, however, where the "dummy target" was missed, the output from inverter is low and the indicator 240 is not lit. The "dummy missed" indication also results in a high input at terminal b of gate 212, thus switching the output of gate 212 to a low state which, in turn, is applied at the input terminal b of NAND gate 242. This generates a high output state from gate 242 which is passed through OR gate 154 and is employed to actuate multivibrator 156, to step the card reading mechanism and begin a new cycle of operation.

Where the dummy target has been "seen" the high output from multivibrator 218 is applied to input terminal b of gate 210 resulting in a low output from that gate. This actuates the "dummy seen" indicator light on the panel which advises the operator that the subject is moved his eyes in a search for the target or is otherwise being uncooperative in the test. It also switches AND gate 242 through line 241 to pulse multivibrator 156 and advance the card reading mechanism.

After the foregoing arrangement has completed its cycle of evaluating whether the subject detected or missed a real or dummy target and a photographic plot of the seen or missed points has been made, the card reader is sequenced to its next position to read the next column of digital information from the preprogrammed card and begin a new cycle of operation.

When the target image is presented, the inputs to terminals c of gates 210, 212 will be low resulting in a high output from these gates into NAND gate 242. If the real target was seen the low output from gate 214 will be inverted at inverter 244 and the resulting high signal will be applied to an input of NAND gate 246. In most instances (except as described below in connection with operation of the vernier logic circuitry) the other input to gate 246 will also be at a high state, resulting in a low output from gate 246 which applied to terminal c of gate 242 thus causing a high output pulse to be applied to multivibrator 156 through OR gate 154 to advance the card reader and begin a new cycle is described above.

Where an actually presented target has been missed (assuming that the device is not being operated in its vernier mode) gate 242 is switched by switching its input d low. This results from the low output of NAND gate 254 when an actual target has been missed. Input b to gate 254 is set high when not operating in vernier (as will be described). Input a to gate 254 is controlled by the output from gate 260. NAND gate 260, in turn, has one input a set high when not operating in the vernier mode through the high state in line 413 which is inverted, at inverter 261 to a low output state which, in turn, is applied to input b of gate 263 maintaining the output of gate 263 high which is applied to input a of NAND gate 260. When an actual target has been missed, output of gate 216 switches low resulting in a high output pulse from NAND gate 260 which switches gate 254 low and in turn switches NAND gate 242.

As will be described more fully with regard to the vernier logic circuitry, when in the vernier mode, a series of targets are presented in a programmed sequence which is incorporated into the logic circuitry itself and is not embodied in the preprogrammed digital input information. For this reason, the card reading and stepping mechanism must be disabled while the vernier sequence is being performed. Whether the vernier cycle is to be employed in a given test is controlled manually by the operator at a switch at the control panel. Once the switch has been set by the operator, the vernier circuit will operate automatically in response to a subject having missed a real target and the card reading mechanism will be disabled. The card reading mechanism is disabled by maintaining a low output from gate 242. Inputs a and b of gate 242 are maintained at a high state when the target image is actually presented and missed. This results from the high output of gate 246 which, in turn, results from the low output of inverter 244 which, in turn, results from the high output of gate 214 when an actual target has been missed. Input d of gate 242 also is maintained at a high state when an actual target is missed and when operating in the vernier mode. To this end, the manual vernier switch operates a flip-flop 248 which, when the vernier is "in", is at a high output state. The high state from flip-flop 248 is applied to line 250 and is inverted through inverter 252 and the resulting low state is applied to input b of NAND gate 254. The resulting high output from gate 254 is applied at input d of gate 242 thus disabling that gate. After the device begins operation of the vernier mode, inputs c and d to gate 242 are maintained at a high state, thus maintaining the card stepping and reading mechanism 162 disabled throughout the vernier operation, which results from line 413 being switched to a low state. This maintains the output from gate 246 into input c of gate 242 high. The output from gate 254, which is applied to input d of gate 242 also is maintained high as a result of the low output from inverter 252 which occurs when operating in the "vernier in" mode.

With the card advancing and reading mechanism disabled the presentation of the vernier target images is initiated by an output pulse from monostable multivibrator 256 as will be described more fully herein. The input to multivibrator 256 is dependent on whether the device is being operated in a "vernier in" mode and also whether a real target has been missed. When operating in the "vernier in" mode, the high state in line 250 is fed into input b of NAND gate 258 to enable that gate. When an actually presented target is missed, the output from gate 216 switches low which, in turn, switches the output from NAND gate 260 high thus switching gate 258 to its low output state. This is inverted at inverter 262 and the resulting pulse is employed to trigger multivibrator 256 and pulse line 266 to begin the functioning of the vernier control logic as will be described.

Should it be desired to stop the machine at any time this may be done by operating panel stop switch 116 which controls a flip-flop 171 to the disable gate 172 and preclude further sequencing of the control logic.

DESCRIPTION OF POSITIONING LOGIC

Figure 10:
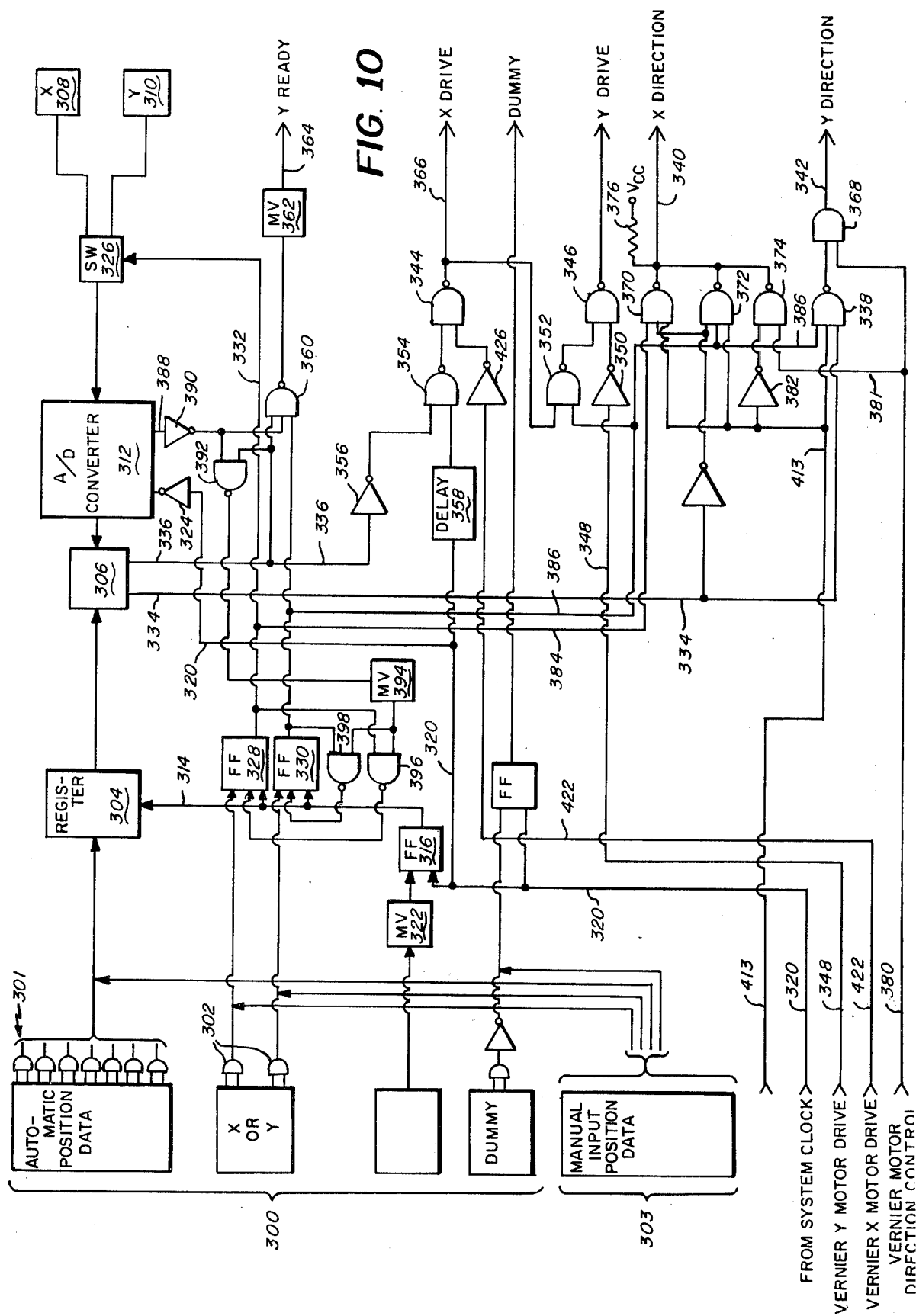
FIG. 10 is a schematic illustration of the electronic logic circuitry for controlling the positioning of the mirror mechanism.

The circuitry for controlling the position of the mirror 26 includes means for both manually and automatically feeding digital information into the machine regarding the desired attitude of the mirror and/or whether a particular target is to be a real or dummy target. The mirror positioning logic receives inputs, selectively, from the vernier control circuitry as well as from the programmed digital information card or tape. As mentioned above, when operating in the vernier mode the sequential positioning of the mirror is a function of the circuitry incorporated into the vernier circuit itself. However, when the position of the mirror is to be controlled by the digital information on the program card or tape, a separate input to the positioning logic is employed. For this purpose, and as shown in FIG. 10, the card reader indicated generally at 300 includes a plurality of output gates 301 which are set to a state corresponding to the information read by the card reader and which corresponds to the target coordinates. This data is transferred to a seven bit register 304 which stores the digital information regarding the particular coordinates of the intended target location. The register 304 feeds a comparator 306. The comparator 306 also receives feedback input corresponding to the actual position of the X and Y stepping motors 70, 80 at any given time. To this end, step motors include follower potentiometers 308, 310 which step with the motors 70, 80 and are employed to feed back, in analog form, a signal corresponding to the position of their respective step motors 70, 80. The analog information is fed through an analog-to-digital converter 312 and the output from the A/D converter is fed into the comparator 306. As will be described below, the X and Y step motors 70, 80 are driven by the output pulses from a system clock in incremental steps which, in cooperation with the gearing selected, will cause the target image on the screen to shift 1°. The output from comparator 306 is employed to terminate driving of the step motors when they have reached a position corresponding to that which was fed into register 304 in digital form.

It may be noted that in the described embodiment of the invention the digital information for a particular intended mirror position is stored on a conventional card having rows and columns of digital data and in a manner in which each column has information relating to either the X or Y position. Whether a particular seven bit digital word read by the target coordinate portion of the card reader relates to an X or Y coordinates is so identified by a bit in the column being read. Thus, card reader 300 also includes a section including output gates 302 which are set, alternatively, to a high or low state depending whether the information which relates to X or Y coordinates. It may be noted that the invention also includes manual means for positioning the target location, indicated generally at 303 and having controls at the control panel.

When operating automatically the card reader will first read a data column relating to the intended position of one of the step motors (the Y motor) and then, after that function has been carried out, the card reader will be advanced to read the next column and carry out the positioning instructions with regard to the other step motor (the X motor).

When a column of digital information is read at reader 300 or fed in at manual input 302, it is entered into the register 304 when the register 304 is pulsed through line 314. Line 314, in turn, carries the output from flip-flop 316 which, in turn, is pulsed by the system clock 318 through line 320, flip-flop 316 having been previously set by multivibrator 322. The starting pulse from the system clock 318 is also applied, through inverter 324 to A/D converter 312 to initiate its operation. The A/D converter 312 is selectively fed with analog information from either of the follower pots 308, 310 as controlled by a switch 326. The position of switch 326 is in turn controlled by the digital input information which also includes in each column data indicative of whether the particular column or manual input relates to positioning of X motor 80 or Y motor 90. The "X or Y" motor identification data is applied to a pair of flip-flops 328, 330. Digital information indicating a column of X information indicating a column of X information relating to the intended position of motor 80 will actuate X flip-flop 328 which, through line 332 operates switch 326 to connect the A/D converter 312 to the X motor follower pot 308. In the absence of an output pulse from X flip-flop 328, switch 326 will normally be in a position which connects the output from the Y follower pot 310 to the A/D converter 312.

The direction in which the step motors 70, 80 are driven is controlled by output 334 of comparator 306. Comparator output 334 controls the state of lines 340 and 342 which are connected to the X and Y step motors 80, 90, respectively to switch the polarity of each motor in accordance with the desired drive direction. Thus, comparator output 334 is low at all times except when the digital information in register 304 is greater than that indicated by the output A/D converter 312. The number of incremental steps which the motors 70, 80 are driven is controlled by comparator output 336 which, in turn, controls the outputs of NAND gates 344 and 346 respectively. Gates 344 and 346 are connected to the motors to drive them one increment for each output pulse. Output 336 of comparator 306 remains low at all times except when the outputs from storage register 304 and A/D converter 312 are equal, in which case comparator 306 produces a high output pulse in line 336.

Assuming that the digital input data in register 304 relates to a Y position coordinate, switch 326 will direct the feedback of analog motor position information from the Y follower pot 310 to the A/D converter 312. This will be compared at comparator 306 with the position data in register 304 which will be entered into the register 304 in response to the output pulse from flip-flop 316, the A/D converter 312 being simultaneously pulsed through line 320 to begin its operation. When the Y information in register 304 if greater than the output from A/D converter 312, the output 334 from comparator 306 will be high, which will result in a low pulse from NAND gate 338. The other inputs to gate 338 also are high, line 413 being high when the system is not operating in vernier and line 386 being pulsed high in response to switching of Y flip-flop 330 as is the case when the digital data relates to Y positioning information. The low output from gate 338 is employed to maintain the polarity of the drive pulse applied to Y step motor 80 to drive it in one direction as will be described. Conversely, if the digital positin information in register 304 is not greater than the output from A/D converter 312, output 334 from comparator 306 will switch low which, in turn, will switch the output of gate 338 to high, thus reversing the polarity of the pulse applied to Y step motor 80 and, therefore, reversing its direction of rotation.

The number of drive pulses received by the Y step motor 80 from the system clock is controlled by NAND gate 346. One input to gate 346 is a function of whether the machine is in a vernier sequence, and, when not, line 348 is low which, when inverted through inverter 350, is applied as a high input to gate 346. The other input to gate 346 is controlled by NAND gates 352, 344 and 354. As long as the outputs from register 304 and A/D converter 312 are not equal, line 336 will be at a low state which, when inverted through inverter 346 will apply a high input to gate 354. The other input to gate 354 is pulsed high by the system clock 318, through line 320 and through a delay circuit 358 to cause a low output from gate 354. This, in turn, results in a high output from gate 344 which produces a low output from gate 352. The low output of gate 352 results in a high output pulse from gate 346 to drive the Y step motor 80 one increment. Delay circuit 358 is of conventional design and permits the analog feedback information from the follower pots 308, 310 to be fed through A/D converter 312 and converted to digital information usable in the circuit.

In the foregoing manner a high output pulse will result from gate 346 each time the clock 316 pulses to step the Y motor 90 until the information in register 304 is equal to the output from A/D converter 312. When that occurs, the output 336 will switch to a high state, switching NAND gate 344 to a low output and thus terminating further stepping of the Y step motor 80. In addition, when line 336 is pulsed to its high state, this pulse is applied to NAND gate 360 which then switches low, triggering monostable multivibrator 362. The output pulse from multivibrator 362 is connected through line 364 to multivibrator 156 of the control circuitry to step the card reader to the next column of digital information which will bear data corresponding to the other (X) coordinate of the intended target image.

It may be noted that when the Y step motor 80 is stepped to its intended position in response to each high output pulse from gate 344, that high output pulse also is directed through line 366 to the X step motor 70 to drive it simultaneously with the Y motor 80. This mode of operation is employed because of the special construction of the mirror positioning mechanism shown in FIGS. 2–7. The construction of that mechanism is such that operation of the Y step motor 80 alone will cause the yoke 56 to rotate which will move the mirror 26 to a position in which the reflected light beam would shift horizontally as well as vertically on the target screen. For example, rotation of the Y step motor 80 in a direction indicated by the arrow +Y in FIG. 5 and 6 would cause the yoke to rotate in the direction indicated by the arrow +Y in FIG. 4. Because the surface of the mirror lies at an angle to the axis of rotation of the yoke, rotation of the yoke in the +Y direction will also cause the mirror to pivot to an attitude to cause the target image to be shifted not only in the +Y direction but also to the left in a −X direction on the projection screen 38 as indicated by the corresponding ±X, ±Y arrows in FIGS. 1 and 2. By simultaneously operating the X step motor 70 in a direction opposite to that which is caused by the Y step motor (here +X), the X component of Y step motor movement can be compensated for. The positioning logic circuitry is arranged so that if the Y step motor 80 is driven a direction to shift the target location up (+Y) and to the left (−X) and the X motor 70 is also driven in a direction which will shift the target image to the right (+X). As will be described, a high output in line 340 will switch the polarity of the X step motor 70 to shift the target image to the left (−X) and a high output in line 342 is effective to switch the Y step motor 80 to shift the target image up (+Y) and to the left (−X), the outputs at lines 340 and 342 would be opposite when the mirror is being positioned to a Y coordinate. The opposite polarity in lines 340, 342 will cause the X step motor 70 to be driven in a +X or −X direction which is opposite to that component of the −Y or +Y direction of the mirror movement which would cause shifting of the target image along an X direction as the yoke is rotated.

The polarity of the pulse applied to Y step motor 80 is controlled by AND gate 368 and the polarity of the pulse applied to X step motor 70 is controlled by NAND gates 370, 372, 374. The outputs from NAND gates 370, 372, 374 are connected in common to a termination resistor 376 which provides an OR function for that combination of gates. When not operating in the vernier mode, line 413, which is connected to the vernier control circuitry in a manner described below, is at a high state. The high state of line 413 is inverted at inverter 382 and the resultant low state is applied to gate 374 thus maintaining its output high at times when the system is not in vernier and the mirror attitude is being determined by the digital input data. The high state of line 413 is also applied to an input of each of gates 370, 372 to enable them to be switched to high or low outputs depending on the state of the other inputs to those gates as will be described below. The high state at line 413, when not in the vernier mode, is also applied to an input of AND gate 368 which enables the gate to be switched, depending on the output from NAND gate 338. Switching of gates 370, 372 and 368 are dependent on the output 334 from comparator 306 and on whether the mirror mechanism 12 is being positioned to a Y coordinate or an X coordinate. When positioning the mirror to a Y coordinate and assuming that the output 334 from comparator 306 is high, all the inputs to gate 338 will be high, switching the output of gate 338 low to maintain a low output from gate 368 to set the polarity of the Y step motor 80 in a direction which will shift the target image down (−Y) and to the right (+X). The X step motor 70 is driven in a compensating direction (−X), to shift the target image to the left, because the high state at line 334 will result in a high output from each of NAND gates 370 and 372. Conversely, if the intended Y coordinate were such that the state of line 334 was low, the output from NAND gate 338 would be high, thus switching AND gate 368 high and directing the Y step motor 80 to shift the target image up (+Y) and to the left (−X). The X step motor 70 would be driven in a compensating direction (+X), to shift the target image to the right, by a low output in line 340 which results from all high inputs to NAND gate 372, switching its output low with a resultant low signal at line 340.

After the mirror has been shifted to the new Y coordinate and the card reader has been advanced as a result of the pulse in line 364, the next column on the card will include data relating to X positioning information and will trigger flip-flop 330. This switches switch 326 to connect A/D converter 312 with the X follower pot 308. In the manner similar to that described above, the gates 370, 372 and 374 result in an output at line 340 which is dependent on comparator output 334. However, when processing X positioning information the high output from flip-flop 328 is applied through lines 384 to an input of gate 370. A second input to gate 370 is maintained high by line 413. The output of gate 370 thus depends on the input 334 from comparator 306. Gate 372, which, during the positioning of X data, has a low input from Y flip-flop 330 will remain in a high output state at all times as will gate 338 which is also connected through line 386 to the otuput from Y flip-flop 330. Thus, when the output from comparator 306, in line 334, is high, the outputs from each of the gates 370, 372, 374 will be high which will direct the X step motor 70 to shift the target image to the left (−X). When the comparator output 334 is low, however, all the inputs to gate 370 will be high, switching its output low and resulting in a low state in line 340 which sets the polarity of the X step motor 70 to shift the target image to the right (+X).

With the polarity for the X step motor 70 set, regular pulses from the system clock will result in high output pulses from gate 344. When the feedback from the X step motor 70 indicates that the motor 70 has reached the intended position, the output from comparator 306 at line 336, switches high which will switch the output of gate 344 low thus terminating further stepping of the X step motor 70. It should be noted that when the mirror 26 is being positioned with respect to X coordinate information, the Y step motor 80 is disabled because of the low output from gate 346. This results from high input to gate 346 from inverter 350 (when not operating in vernier) and a high input to gate 346 from gate 352. The output from gate 352 is maintained high during the X coordinate positioning because of the low input to that gate by line 386 from Y flip-flop 330 which has a low output state during the processing of X coordinate information.

Where a dummy target is to be presented neither of the X or Y flip-flops 328, 330 are actuated and the positioning system remains inactive.

It may be noted that X and Y flip-flops 328, 330 are self-resetting. When the A/D converter 312 has cycled, its "busy" output at line 388 switches low which, when inverted through inverter 390 switches gate 392 which, in turn, actuates multivibrator 394. The output from multivibrator 394 operates gates 396, 398 which are effective to reset the Y flip-flop 330 and X flip-flop 332, respectively.

The foregoing description of the positioning control has related to its operation when the system is not within a vernier cycle. When in a vernier cycle the number and direction of steps for each stepper motor is controlled entirely and independently by the vernier control circuitry.

DESCRIPTION OF VERNIER LOGIC

As mentioned above when it is desired to examine more closely the regions of the subject's visual field about actually presented targets which were missed by the subject, the panel switch 122 is set to the "vernier in" mode of operation. This enables automatic operation of the vernier cycle in response to the subject having missed an actual target and disables the card reading and advancing system until the vernier target presentation has been completed. When operating in the "vernier in" mode, a signal from the decision logic indicating that the subject has missed a real target image will cause automatic actuation of the vernier control logic to automatically present a plurality of target images in a predetermined array and sequence and in close proximity to and surrounding the location of the target image which is missed. FIG. 9A shows the relative location of the vernier target images with respect to the primary target image which was missed. In the preferred embodiment, three vernier targets are presented in a triangular configuration about the primary target image location located at 400 in FIG. 9. The first of the three vernier points to be presented in the sequence V1 is located 1° directly above the primary target location 400. After vernier image V1 has been presented and the subject's eye position and movements evaluated, the vernier control circuitry causes the mirror to be repositioned to present vernier point V2 which is also spaced 1° from primary target location 400 but below and to the left of location 400 as indicated. The procedure of evaluating the subject's eye movements with respect to vernier target image V2 is performed and the vernier control logic then causes repositioning of the mirror to present vernier target image V3. Vernier image V3 is spaced 1° from the primary target image 400 and is downwardly and to the right of that location to define the triangular spacing of the three vernier points V1, V2 V3.

By presenting a plurality of vernier targets in sequence, fine mapping of the subject's visual field about the region of a missed point is achieved and may show a general boundary line of the subject's scotoma. For example, if the vernier presentation indicates that the subject missed vernier points V1 and V2 but saw vernier point V3, this would indicate that the boundary line of the particular scotoma in question would extend somewhere between vernier point V3 and a line drawn between vernier points V1 and V2 is indicated by phantom by the line 402 in FIG. 9. If the subject missed all three of the vernier targets V1, V2 and V3 this would indicate that the boundary of the scotoma was somewhere outside all of the vernier points. Conversely, if the subject saw all three vernier points this might indicate that the scotoma is quite small and is located closely about the primary target image location 400. It may be noted that while the illustrative embodiment of the invention shows a vernier pattern of only three points, a more fine mapping of the scotoma boundary could be achieved by employing more than three vernier points, as suggested in FIG. 9A in which there are six vernier points presented which would provide still further fine mapping of the scotomic boundary. However, three vernier points are adequate for most testing purpose.

Figure 11:
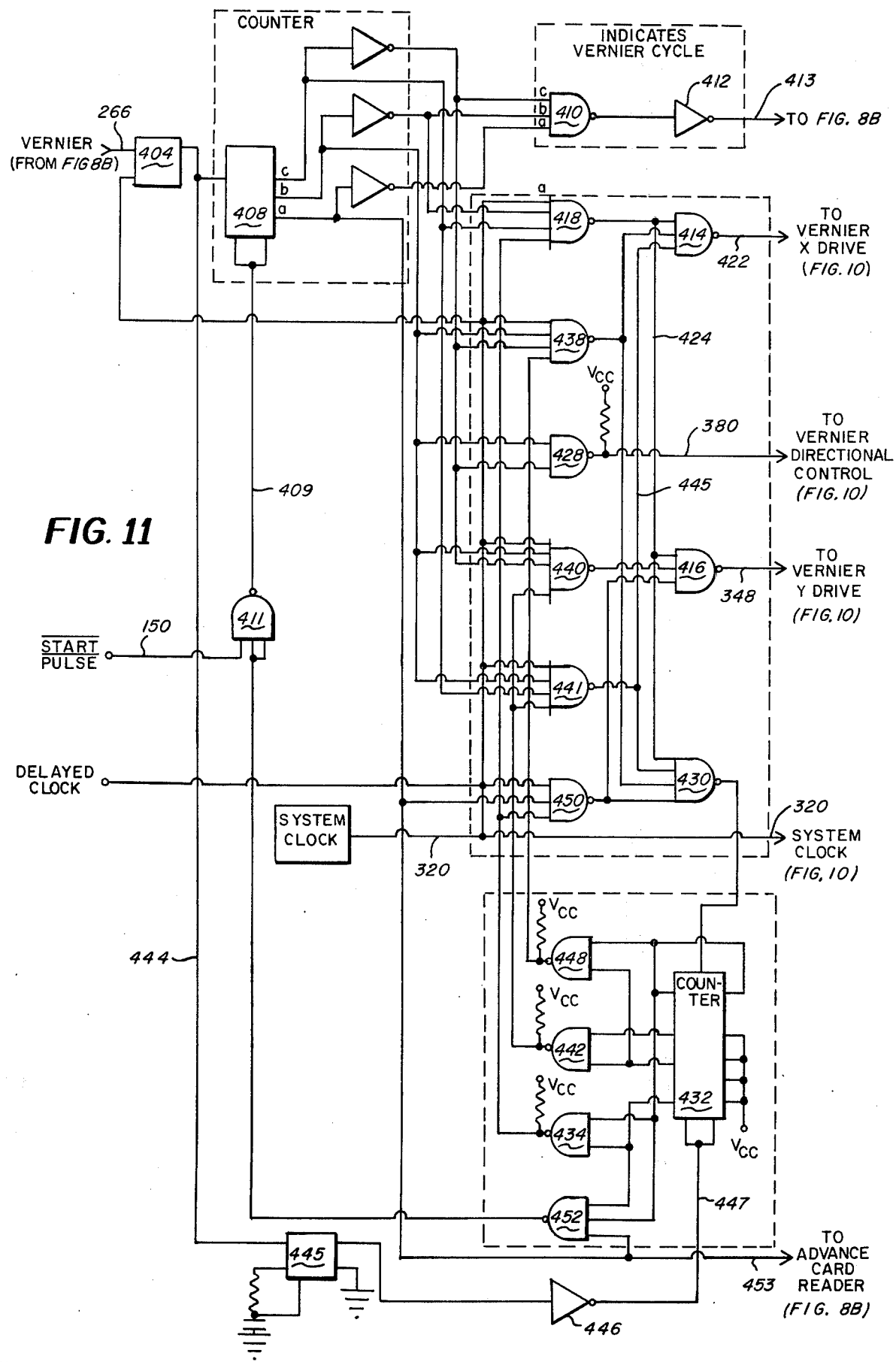
FIG. 11 is a schematic illustration of the electronic logic system for controlling presentation of the vernier target images.

The vernier sequence is begun in response to a missed target by an output pulse from multivibrator 256 (FIG. 8B) which is applied to pulse flip-flop 404 (FIG. 11) through line 266. The other input to flip-flop 404 is synchronously controlled by the system clock 318 to produce an output pulse from flip-flop 404 synchronously with the timing of the vernier system as controlled by the system clock. The output pulse from flip-flop 404 is fed into a three bit digital counter 408 having both positive and inverted outputs. It may be noted that counter 408 is rezeroed through line 409 at the beginning of each operational sequence by its connection to line 150 through gate 411. The inverted outputs are connected to the three inputs of NAND gate 410, the output of which is connected to line 413 of the control logic and position logic circuits described above. Thus, where the system is not operating in vernier or, if in vernier and a target was seen, there is no output pulse from multivibrator 256 and the flip-flop 404 remains in the low output state. As a result each of the three counter outputs a, b, c will be at a low state (000) which, when inverted and fed into NAND gate 410 will result in a low output which may be inverted through inverter 412 to a high state which is applied to line 413. As described above, when line 413 is high gates 246 and 254 are disabled and cannot control switching of gate 242.

When a target is missed the first vernier pulse from multivibrator 256 is applied to flip-flop 404. The counter 408 switches to a (001) digital state which results in input a to gate 410 being switched low. This results in a high output from gate 410 which is inverted to a low state through inverter 412 to switch line 413 to a low state. As described above, when line 413 is switched low, gate 246 is switched to produce a high output which further precludes operation of the step card reader multivibrator 156 during the vernier sequence. Similarly, because the panel switch and flip-flop 248 is set to the vernier position, the output from gate 254 is high. In addition, line 413 is connected to an input of each of NAND gates 370, 372 and 338 of the position logic (FIG. 10) to maintain their high outputs and disabling them from switching to low output during the vernier cycle. The high output from NAND gate 338 enables AND gate 368 to be controlled directly by the vernier circuitry through line 380 as will be described below. Line 380 is also connected through line 381 to an input of gate 374 to control its output in response to the vernier circuit. It should be noted that the other input to NAND gate 374 is enabled by high signal from an inverted input, through inverter 382 from line 413. It may be noted that during operation of a vernier cycle one of the inputs a, b or c to gate 410 will be low, which maintains the low state in line 413.

When counter 408 has received its first pulse from flip-flop 404 and has been switched to a (001) digital configuration the X and Y steps motors 70, 80 are driven to a position which will orient the mirror 26 to reflect the light target at the first vernier position V1 which, in the illustrative embodiment, is 1° above the location of the missed target 400. This requires the Y step motor 80 to be advanced to move the mirror to reposition the image one step upwardly (+Y) and to the left (−X) and the X motor 70 to compensate one step to the right (+X). The number of pulses applied to the step motors is controlled by switching X NAND gate 414 and Y NAND gate 416 to develop output pulses in response to and for the desired number of output pulses from the system clock 318. For example, with the counter 408 set to a (001) output all but input terminal a of NAND gate 418 will be high. When the system clock 316 pulses input a, through line 420, the output from gate 418 will be switched to low which will result in an output pulse from X NAND gate 414 and, through line 424, a high output pulse from gate 416. The output of gate 414 is connected through line 422 to the position logic circuit. As shown in FIG. 10, a high output in line 422 will be inverted to low at inverter 426 and that low signal switches the output of gate 344 high to pulse the X step motor 70. The high output from gate 416 is connected through line 348, through inverter 350 (FIG. 10) to pulse NAND gate 346 high and drive the Y step motor 80 one increment.

The direction in which each of the step motors is driven for the first vernier point is controlled by the state of line 380. Line 380 is connected to the output of NAND gate 428 and its state is dependent on the output from counter 408. When counter 408 receives its first pulse to begin positioning of the first vernier point the input to gate 428 from output b of counter 408 will be low thus maintaining line 380 at a high state. This, in turn, results in a high output pulse from gate 368 to direct the Y step motor to drive the mirror in a +Y, −X direction (up and to the left as seen on the screen) and results also in switching of gate 374 resulting in a low output which will direct the X step motor 70 to drive the mirror in a compensating +X direction to shift the target image location to the right.

The output pulse from gate 418 also is applied to NAND gate 430 which, in turn, drives a two-bit counter 432. When the output from gate 418 switches low in response to termination of the clock pulse, output from NAND gate 430 switches high, pulsing counter 432. The output from counter 432 switches NAND gate 434 so that its resultant low output will be applied to an input of gate 418 through line 436 thus switching gate 418 back to its high output state which, in turn, switches vernier control gates 414, 416 back to their low output state and terminates the positioning of the mirror at the first vernier point. With the mirror having been positioned to the first vernier point V1 within the delay of multivibrator 164, the resetting of multivibrator 164 to its low output state pulses gating circuit 170 through line 168 (FIG. 8A) to control the projection shutter, projection light, the camera shutter, record light in the same manner and sequence described previously. The subject's response to the presentation of the first vernier point V1 is monitored by the photocells 92, 94 and the decision logic circuitry determines whether the subject saw or missed the first vernier point. Depending on whether the photographic recording system is set to record seen/record missed points, a photographic plot of the subject's response to the presentation of the first vernier target image may be recorded. Whether the subject saw or missed the first vernier point, after his response has been evaluated multivibrator 256 is then pulsed to continue the vernier sequence. This results from the output pulse from gate 258 each time either of gates 214 or 216 are switched. It should be noted that each time counter 408 is advanced from the output from flip-flop 404, counter 432 is reset to a (00) state through line 44, flip-flop 445, inverter 446 and line 447.

The foregoing sequence of automatically entering into the vernier mode and positioning the mirror to direct the target image to the first vernier location all takes place within the delay constant of multivibrator 164 which may be of the order of slightly over one second.

After the first vernier target image V1 has been presented, and it has been determined whether the subject has seen or missed it, and whether the response should be photographed, the second vernier point is presented. As can be seen from FIG. 9, this requires movement of the Y step motor 80 to shift the target image two increments downwardly (−Y) and to the right (+X) and three incremental steps of the X step motor to the left (−X). When multivibrator 256 is again pulsed to cause the output from flip-flop 404 to advance counter 408 to the next digital state (010), the output from counter 408 switches NAND gates 438, 428, 440 to each produce low output pulses which, in turn, switches X and Y gates 414, 416 to produce high output pulses synchronously with system clock 316. The switching of NAND gate 328 produces a low pulse in line 380 which is effective to reverse the polarity of the pulses applied to the step motors thus reversing the direction of the X and Y step motors. By switching the state of line 380 low, the output from AND gate 368 will switch low causing the polarity of the drive pulses which are directed to the Y step motor to shift the target image location downwardly (−Y) and to the right (+X). The low pulse in line 380 also is applied through line 381 to gate 374 switching its output high which, in combination with the high outputs from gates 370 and 372 result in a high state in line 340 which will direct the X step motor 70 to shift the target image location to the left (−X). The X and Y motors are pulsed in the manner described above with counter 432 being advanced for each pulse from the system clock. When the counter 432 has been pulsed twice and advanced to a (10) digital state NAND gate 442 switches from its high state to produce a low output pulse which is applied to an input of gate 440 thus switching that gate to a high output which in turn switches gate 416 low and terminates further operation of the Y step motor 80 after two incremental steps. The X drive gate 414, however, is driven one more time until counter 432 registers the third digital state (11) which causes NAND gate 448 to switch to a low output, causing a high output from gate 438 which, in turn, disables X gate 414 to terminate operation of the X step motor 70. The target is then presented at the second vernier point V2 and the decision and control logic run through their respective sequences as described above. It may be noted that when presenting the second vernier target the operation of multivibrator 164 is controlled by the output of multivibrator 256 through line 257 and not by multivibrator 156 which is disabled during vernier operation.

In order then to present the third vernier point it may be seen (FIG. 9) that the mirror must be moved to shift the target image location two increments to the right (+X). In the illustrative embodiment this requires operation of the X step motor alone. Thus, when the counter 408 has been pulsed to its next digital state (011) gate 428 will switch to a high output again reversing the polarity of the pulse which is applied to the step motors through line 380. The Y drive gate 416 remains in a low output state as all of its inputs are high. X drive gate 414 is switched through line 445 to produce a high output pulse as the output from gate 441 switches to low in response to all high inputs to gate 441, thus stepping the X motor. When counter 432 has been pulsed twice, the output from gate 442 switches to low, thus switching gate 441 to a high output which switches X drive gate 414 low and terminates further stepping of the X drive motor. With the mirror positioned to show the third vernier point, the third vernier target image is presented and the control and decision logic perform their respective functions.

After the three vernier points have been presented, it then remains for the mirror to be repositioned to the location of the original target image which was missed and which initiated the vernier sequence. This, in turn, requires that the Y motor be stepped one increment up (+Y) and to the left (−X) while the X motor is maintained inoperative. When counter 408 is pulsed, for the fourth time, and is advanced to the (100) state, the inputs to X gate 414 remain high thus maintaining X step motor inoperative. The Y drive gate 416, however, switching to a high output state because of the low input in response to the low input from fate 450. Gate 450 is switched to a low output by reason of the high input to it from counter 408. After NAND gate 430 has pulsed counter 432 to indicate one pulse, NAND gate 452 is switched high and, through line 454 resets counter 408 to its initial digital state (000). Resetting of counter 408 to the (000) digital state, returns line 413 to a high state. The (100) state of counter 408 also causes gate 453 to be pulsed and which passes through OR gate 154 switches multivibrator 156 to advance the card reader and resume the presentation of the primary targets.

DESCRIPTION OF THE DECISION LOGIC

The position and movement of the subject's eyes are monitored by the eye imaging techniques described in U.S. Pat. Nos. 3,583,794 and 3,689,135 in which the image of the subject's eye is projected onto a screen and in which photocells 92, 94 are located on the screen to be responsive to the position and movement of the eye image. The vertically spaced photocells 92 detect variations in the vertical position of the subject's eye (including movements of the eye lid) and the horizontally spaced photocells 94 detect changes in the subject's horizontal eye position. The outputs from the horizontal and vertical photocell pairs result in a signal which is indicative of both magnitude and direction of the subject's eye movement. The decision logic circuitry is designed to discriminate between photocell outputs which are characteristic of the subject having actually seen or missed the presented target, hunting eye movements and blinks.

Figure 12A:
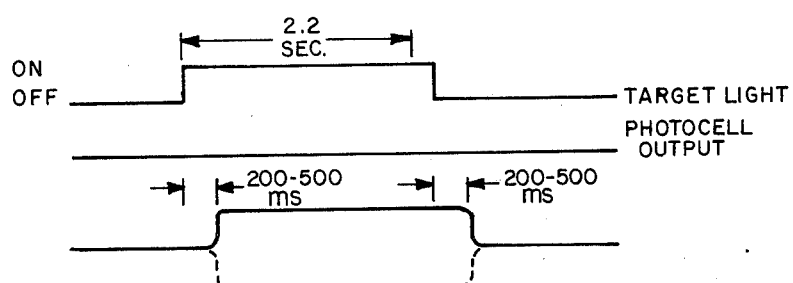
FIG. 12A is a DC plot of a subject's response when an actually presented target has been missed.

FIG. 12A is a DC representation illustrating the relationship between the presentation of the target image and a subject's target missed response as indicated by the output from the photocells. Where the subject's eye does not move during presentation of the target there is no change in output from the photocells.

Figure 12B:
FIG. 12B is a DC plot of an ideal "target seen" response.

FIG. 12B illustrates an ideal response in which the subject has actually seen the target image. Typically, there will be a slight delay from the time in which the target is presented to the time in which the subject's eyes actually move and the response may be delayed, for example 200–500, milliseconds. Also, when the sighted target image is turned off a similar delay will occur in the subject's returning his eyes to the central fixation target. It may be noted that the photocell output may be positive or negative depending on the direction of movement of the subject's eyes. As will be described in connection with the decision logic circuitry, the direction of eye movement is not critical in the particular embodiment shown, the magnitude being the primary consideration.

Figure 12C:
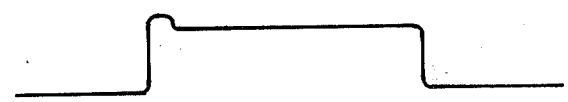
FIGS. 12C and 12D are DC plots of a three saccade response in which the subject initially detected the target but required a minor correctional saccade to focus directly on the target.
Figure 12D:
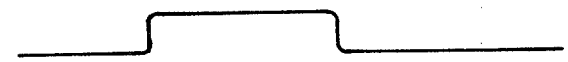

FIG. 12C illustrates the photocell output in a situation where the subject has sighted the target but was unable to control his eye movement to direct it precisely to the target image in a single saccade. The photocell output indicates a first substantial eye movement to the general vicinity of the presented target image and a second, minor correctional movement. For example, the first saccade may be of the order of 5° or more, depending on how far the target image is from the central fixation point and the second correctional saccade may be of the order of 3° or less. FIG. 12C shows a minor correctional saccade in the same direction as the first saccade and FIG. 12D shows a minor correctional saccade in an at least partly reversed direction. Both responses indicate an actually seen target.

Figure 12E:
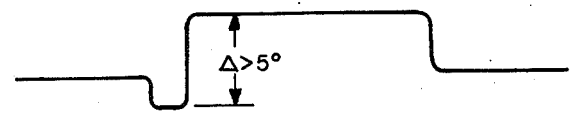
FIG. 12E is a DC plot of a subject's response where the target was detected but where his eyes returned to the central fixation point before the target light was switched off.

FIG. 12E shows a further response which is indicative of the subject having actually seen the target. This response may be considered as an "early return" in which the subject returned his eyes to the central fixation position before the target light was extinguished. This response also is considered as an actually seen target.

Figure 12F:
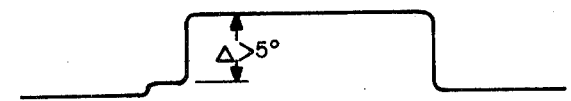
FIGS. 12F and 12G are DC plots of the subject's eye movement where he did not see the target image and moved his eyes to hunt or search for the target.

FIG. 12F illustrates a hunting or searching eye movement in which the difference in magnitude of the photocell outputs between the first and second saccades is substantial, for example, of the order of more than 5°. This may result from a first saccade in a direction which is away from the location of the target image, as shown in FIG. 12F or may result from an eye movement shown in FIG. 12G in which, while the searching saccade and second saccade are in the same general direction, the second saccade is substantial, of the order of more than 5°.

FIGS. 12H shows a typical output from the vertically spaced photocells which results from a blink. The duration of a typical blink is of the order of 30–50 milliseconds and results in a relatively short duration pulse. Of course, a blink may occur at any time, whether the target is being presented or not.

The decision logic circuitry is effective first to determine whether an output from the photocells is the result of a blink. If so, the remaining portions of the decision logic are disabled from further evaluating that photocell output.

Figure 12G:
Figure 13:
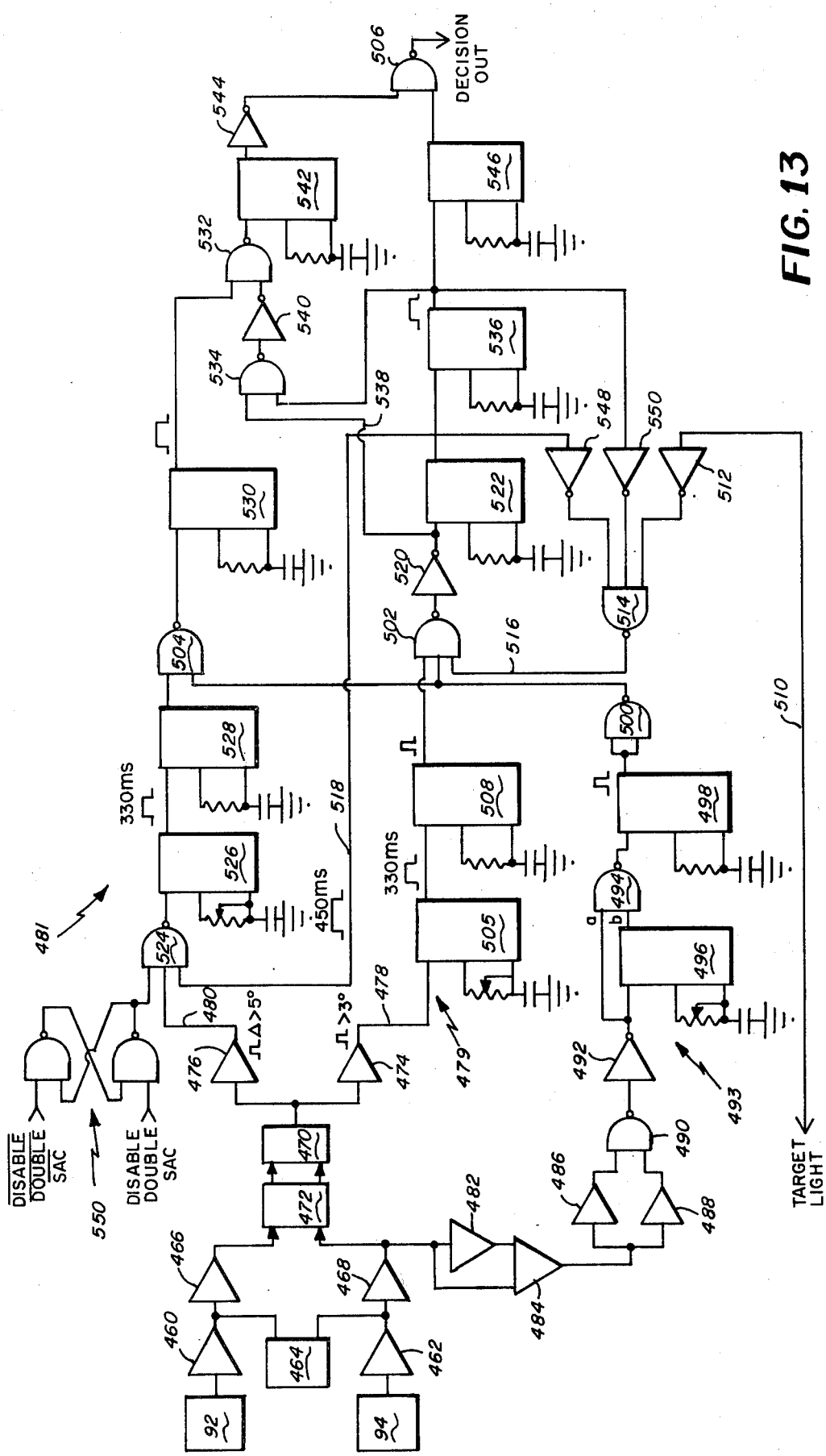
FIG. 13 is a schematic diagram of the decision logic circuitry.

As shown in FIG. 13 the outputs from the horizontal and vertical photocell pairs are amplified at amplifiers 460, 462 respectively. The amplified signals may be coupled to a strip chart recorder 464 if desired to provide a permanent charted D.C. record of the subject's eye movements. The outputs from amplifiers 460, 462 are fed through buffer amplifiers 466, 468 and these signals are coupled to an absolute value adder 470 through AC couple 472. Where the amplified signals from the photocell pairs are DC, the AC couple is effective to overcome the effect of any long term drift which might be inherent in the system as well as to overcome the effect of any slight head shift of the subject during the test. The absolute value adder insures that a positive output from one pair of photocells will not be negated by a negative output from the other pair of photocells but, instead, results in an output which is the sum of the magnitude of the photocell outputs regardless of their sense. The output from absolute value adder 470 is coupled to a first sense amplifier 474 and also to a second sense amplifier 476. Sense amplifier 474 is selected so that it will pulse line 478 when the amplitude of the input to amplifier 474 corresponds to an eye movement of more than a first predetermined magnitude, for example, 3°. Sense amplifier 476 is effective to produce an output pulse in line 480 in response to an input from adder 470 having an amplitude corresponding to a change in the direction of eye movement of more than a second predetermined magnitude, for example, 5°. The outputs at lines 478 and 480 are employed in the decision logic circuitry to discriminate between the various saccadic movements illustrated in FIGS. 12A–12H in a manner described below.

The decision logic includes three channels including a primary saccade detection channel 479, a secondary saccade detection channel 481 and a blink detection channel 493. Each signal resulting from the output of either or both of the photocell pairs 92, 94 is applied to each of the three channels simultaneously. If the photocell output was the result of a blink the blink detection channel 493 disables the primary and secondary channels 479, 481 from further operation thus disregarding the effect of the blink. If the resulting signal from the photocells 92, 94 was caused by a genuine saccade this is detected by the primary channel 479 which, in turn, is connected to the secondary channel 481 to enable the secondary channel to thereafter detect existence of a second saccade within a predetermined time interval after the first saccade. The output from the first channel is also connected to an output decision gate 506 (as will be described) in a manner which causes that gate to be enabled at a fixed, predetermined time interval after the detection of the first saccade. The state of the other input to decision out gate 506 is dependent on whether the primary and secondary channels 479, 481 have detected the existence of only two or more saccades and the timed relationship of the saccades with respect to the presentation of the target image as well as their magnitude.

More particularly in order to discriminate blinks from other eye movements, the signal from the vertical photocells is connected through buffer amplifier 468 to a sample and hold circuit 482 and also to a comparator 484, the output from the sample and hold circuit 482 also being fed into comparator 484. Comparator 484, in turn, drives a pair of sense amplifiers 486, 488 which produce an output pulse when the output from the comparator is positive and negative respectfully. When an output signal results from the photocells, the decision logic circuit first evaluates whether the output was the result of a blink. If so, the decision logic circuitry is disabled and there is no change in its output. The blink detection circuitry includes a NAND gate 490 having its inputs fed by sense amplifiers 485, 488. The output from NAND gate 490 is inverted at inverter 492. The inputs to NAND gate 474 are normally high which results in a normally high output from inverter 492. The output from inverter 492 thus may be switched by any change of state to either input to gate 490 resuling from a pulse from either of sense amplifiers 486, 488. The output from the inverter 492 is connected directly to an input of NAND gate 494 and also to the other input of gate 494 through a multivibrator 496 having a delay constant of, for example, approximately 330 milliseconds. When either input to NAND gate 490 is low as a result of a signal from the vertical photocells input of gate 494 will remain low, to preclude switching of gate 494 while monostable multivibrator 496 will switch to a high output state.

If the triggering input to NAND gate 490 was the result of a blink, which typically lasts between 30–50 milliseconds, the low output of inverter 492 and input *a* of gate 494 will switch back to high before multivibrator 496 has returned to its low output state. The all high inputs switch gate 494 to a low output which triggers monostable multivibrator 498, switching it to a high output state and switching the output of NAND gate 500 to low. A low state at the output of NAND gate 500 indicates the presence of a blink and disabled NAND gates 502 and 504 which, in turn, precludes any change in output of the decision out gate 506 as will be apparent from the further following description. If, on the other hand, the input to NAND gate 490 was the result of a genuine saccade in which the subject's eye remain fixated for considerably more than 30–50 milliseconds, the direct input to gate 494 will remain low at all times during and after the delay of multivibrator 496 thus leaving gate 94 unactuated and maintaining the output from gate 500 in its normally high state which, in turn, maintains the inputs to gates 502, 504 high and in an enabled state.

If the blink detection channel 493 has detected that the input pulse was the reset of aa genuine saccade, the remaining primary and secondary channels 479, 481 evaluate whether the saccade was the result of the subject's actual perception of the target image or whether it was the result of "hunting" or searching eye movements. When an added pulse from one or both pairs of photocells is fed into sense amplifiers 474, 476 those amplifiers, respectively, evaluate whether the saccade (here the first saccade) was of a magnitude of more than 3° and whether the saccade was a change in eye movement of more than 5°. For example, assuming that a target was presented and was seen, the subject's eye movement of more than 3° results in an input pulse to monostable multivibrator 505 switching its output high. Multivibrator 505 has a 330 millisecond delay function and serves to delay further operation of the portions of the primary channel 479 for a time sufficient to enable the blink detection channel 493 to evaluate whether the pulse resulted from an eye movement or a blink. When multivibrator 505 switches back to its low, stable state, that actuates monostable multivibrator 508 switching its output momentarily to a high state. If the target light was on at the time of the saccade then all three inputs to NAND gate 502 are switched to high. This is accomplished by applying a pulse in line 510 indicating that the target light is on and passing it through inverter 512 and NAND gate 514 to produce a high pulse at input of gate 502, thus enabling that gate as long as the target light is on. It may be noted that while the first saccade may have been of a magnitude which would have also switched the output from sense amplifier 476 to a high state, gate 524 is, at that time, in a disabled state because of the low input, through line 518 from the monostable multivibrator 522 as will be described.

In order to evaluate whether the first saccade was the first of a series of eye movements indicating true perception of the target or whether it was a "hunting" saccade, the decision logic awaits subsequent signals from the photocells to determine whether only a second saccade follows or whether both a second and third saccade follows. Also, where there are three saccades, their relative magnitudes must be evaluated to discriminate between hunting movements (FIGS. 12F, 12G) and acceptable correctional movements (FIGS. 12C, 12D). As described above, saccadic movements of less than a predetermined magnitude for example 3°, are considered to be mere correctional movements. Thus, a pulse resulting from photocells 92, 94 which corresponds to an eye movement of less than 3° will be isolated from the primary and secondary channel, 479, 481 by the sense amplifiers 474, 476 respectively. There being no signal applied to the primary and secondary channels, an eye movement of less than 3° has the same effect as if there had been no eye movement at all thus completely disregarding mere correctional movements.

As indicated at FIGS. 12A–12G, where there has been a first saccade there will always be a second saccade. The second saccade may result from the subject's returning his eyes to the central fixation target (FIGS. 12B, 12E) in which case the second saccade is a final saccade indicating that the subject actually saw the target. However, the second saccade may have been the result of the first time that the subject actually saw the target, in which case the second saccade would be only an intermediate saccade which would indicate that the first saccade would have been a hunting or searching movement (FIGS. 12F, 12G). In order to discriminate between these saccadic movements the invention employs a technique in which the subject's eyes are monitored to detect the existence and magnitude of at least three saccades in which the intermediate saccade or saccades was more than 5° which would indicate that the first saccade was a hunting movement and that the subject did not actually see the presented target.

The foregoing functions are enabled by the switching of gate 502 to a low output state which is the case when the first saccade is not a blink, as described above. The low output from gate 502 is inverted to a high state through inverter 520 and that pulse is applied to monostable multivibrator 522. Multivibrator 522 is switched to its high output state when the output from multivibrator 508 retuns to its low state after generating its short pulse. When multivibrator 522 is switched, its high output is applied to the input of NAND gate 524 which enables that gate and, consequently, the secondary channel 481 to be actuated when the remaining low input of gate 524 receives a high pulse from sense amplifier 476. Multivibrator 522 has a time delay which will maintain its high output state, thus maintaining the secondary channel 481 in an enabled state for a time sufficient to include that in which a second, intermediate saccade would be made. For example, the delay of multivibrator 522 may be of the order to 450 milliseconds. Thus, if the photocells 92, 94 produce a signal indicating a saccade which was a change of more than 5° and during the enabled interval of secondary channel 481, gate 524 will be actuated to switch its output low to low thus actuating blink delay monostable multivibrator 526 which also has a time delay constant of 330 milliseconds. This enables the block detection logic to again evaluate whether the second input signal to gate 524 was the result of a blink or a genuine second saccade. If a blink, the low output at gate 500 of the blink detection logic is applied to an input of gate 504 thus disabling that gate and the secondary channel 481. However, if the signal was not a blink gate 504 will be enabled. When multivibrator 526 switches back to low state, after its 330 millisecond delay, and that pulse triggers monostable multivibrator 528 to produce a short output pulse switching gate 504 low which triggers monostable multivibrator 530 switching its output high. This high output is applied to an input of NAND gate 532 which enables that gate. Multivibrator 530 has a delay constant sufficient to maintain gate 532 in an enabled state for an extended interval ending shortly after the target light has been extinguished. By way of example the delay may be of the order of 2.75 seconds. As described below the other input to gate 533 depends on whether or not there was a third saccade which, in turn, controls the output of gate 532 and the input to decision out gate 506.

The detection of a third saccade is effected by the primary channel 479. After the 450 millisecond delay of multivibrator 522, its output switches low which switchs multivibrator 536 to a high output state. This, in turn, enables one of the inputs to gate 534. Multivibrator 536 has a delay constant which also extends beyond the time that the target lights is extinguished in order to be able to detect return eye movements which often occur after the extinguishment of the target light. It may be noted that multivibrator 530 has a delay slightly longer than multivibrator 536 so that gate 532 may remain enabled and be switchable in the event that gate 534 is switched. If a third pulse is emitted from the photocells, it will, as is the case for each such pulse, be directed to the sense amplifiers 474, 476 as well as to the blink detection circuitry. Multivibrator 505 delays functioning of the primary channel 479 stages until the blink detection channel 493 has an opportunity to evaluate whether the photocell output was the result of a saccade or a blink. Assuming that it was not a blink and that a third saccade was made by the subject, the signal resulting from the third saccade switches the output from inverter 520 high which is applied through line 538 to the other input of gate 534 switching its output low which, is inverted at inverter 540 and is fed as high pulse into an input of NAND gate 532. This results in a low output from gate 532 which switches multivibrator 542 to produce a high output which is inverted at inverter 544 and is fed into decision out gate 506. This will not switch and its 164 in the control logic andits output will remain low thus indicating a "missed target."

When there is no third saccade during the delay of multivibrator 536, this indicates that the second saccade was in fact a final saccade to the central fixation point and was thus an actually seen target. When there is no third saccade the input to decision out gate 506 from inverter 544 is high thus enabling that gate. When multivibrator 536 switches back to its low stable output state this switches multivibrator 546 and the high output pulse from multivibrator 546 switches decision out gate 506 to a low output which, in turn, actuates multivibrator 164 and indicates a target seen.

In some mass testing situations it may be desirable to make a more coarse test, for example, to detect only whether the subject responded at all to presentation of the target image. This may be accomplished by disabling the second channel 481 so that the output from inverter 544 will remain high at all times thus maintaining decision out gate 506 enabled continuously. Any non-blinking eye movement during presentation of the target image will result, ultimately, in a pulse from multivibrator 546 which will switch decision out gate 506 low indicating a response by the subject during presentation of the target image. While this mode of operation does not discriminate between hunting eye movements and true perceptions, it does give a rapid more coarse testing procedure. The second channel may be disabled by switch 126 on the control panel which switches flip-flop 550 to enable or disable gate 524 as desired.

When the subject has actually perceived the target and makes a "normal" response (FIG. 12B) his eyes will fixate on it as long as it is presented (approximately 2.2 seconds). In this event there will be no detected eye movement during the 450 milliseconds that the multivibrator 522 is in its high state. Thus, even though gate 522 is in readiness to be actuated in response to sensed eye movement during the 450 millisecond interval, there is no movement and the input to gate 532 remains low. When the subject's eyes do return to the reference fixation target shortly after the target light has been extinguished from the subject's view the pulse resulting from the saccade, which is channeled to gate 502 causes multivibrator 522 to be pulsed. The high output from multivibrator 522 is inconsequential at this time because multivibrator 536 already is in its high state. When the multivibrator 536 switches back to its low state multivibrator 546 is pulsed to apply a high input to decision out gate 506. The other input of the decision out gate 506 is also high at this time because as multivibrator 536 was switched to its low state, gate 534 switched to a high state which is inverted to low through inverter 540 which maintains gate 532 at a high state thus precluding actuation of multivibrator 542 whose normally low output is inverted at 544 to a high state which is applied to the decision out gate 506. The resulting low pulse from gate 506 is applied through line 470 to the control logic as previously described. As described previously, there may be some instances in which the subject has perceived the target but returns his gaze to the general region of the central fixation target before the target light has been extinguished. Such early return is detected by the foregoing decision logic as a perceived target. Here, the subject's eye movement usually will be after the 450 millisecond delay of multivibrator 522 but before multivibrator 536 has switched back to its low state. This has the same effect as a "seen" response described above.

In order to insure that gate 502 is enabled through line 516 during the extended time interval which includes the interval during which the target is actually presented and a short time thereafter, the output from multivibrator 522 is connected through inverter 548 to an input of gate 514 and the output from multivibrator 536 is connected through inverter 550 to the other input of gate 514 thus insuring a high state in line 516 at all times during operation of the decision logic.

The foregoing mode of operation of the decision logic may be considered as employing a technique in which the extended time interval during which the subject's eye positions and movements are monitored may be considered as divided into successive portions in which each portion begins with eye movement. The number and duration of each such portion of the extended time interval will, of course, depend on the time in which the subject moves his eyes. In addition, an initial segment of each portion of the extended time interval is employed to evaluate whether the particular eye movement was a blink, in which case the eye movement is disregarded as described above.

It should be understood that the foregoing description of the invention is intended merely to be illustrative thereof and that other modifications and embodiments of the invention may be apparent to those skilled in the art without departing from its spirit.

Having thus described the invention what I desire to claim and secure by Letters Patent is:

1. A method of objectively testing the visual field of a subject:
   providing reference fixation target within the subject's visual field;
   thereafter presenting a target image to said subject, at a selected location within the subject's visual field and at a selected angular distance from said reference target, said target image being presented for a determined time interval;

monitoring the position and movement of the subject's eye at least during an extended time interval which includes and which extends beyond said predetermined time interval; and determining whether the subject actually visually detected the presented target image by electronically detecting the number and magnitude of the subject's eye movements during said extended time interval.

2. A method as defined in claim 1 wherein said step of determining whether the subject actually visually detected the presented target image comprises, at least in part:

detecting, within said extended time interval, those of the subject's eye movements having at least three saccades and in which the magnitude of an intermediate of said saccades is more than a predetermined magnitude thereby indicating a hunting eye movement and a missed target.

3. A method as defined in claim 2 wherein said predetermined magnitude comprises approximately 3°.

4. A method as defined in claim 1 wherein said step of determining whether the subject actually visually detected the presented target image comprises, at least in part:

detecting, within said extended time interval, those of the subject's eye movements having at least three saccades and in which the magnitude of the first of said saccades does not differ from said selected angular distance by more than a predetermined magnitude and in which the magnitude of an intermediate of said saccades is no more than a predetermined angle.

5. A method as defined in claim 1 wherein said step of determining whether the subject actually visually detected the presented target image comprises, at least in part:

detecting, within said extended time interval, those of the subject's eye movements having only two saccades, each of which is of a magnitude substantially equal to said selected angular distance.

6. A method as defined in claim 1 wherein said step of determining whether the subject actually visually detected the presented target image comprises:

detecting, within a first portion of said extended time interval, the existence of an initial saccade of a magnitude greater than a first predetermined magnitude;

detecting, within a second portion of said extended time interval, the existence of a subsequent saccade of a magnitude greater than a second predetermined magnitude;

detecting, within a third portion of said extended time interval, the existence of a subsequent saccade of a magnitude greater than said first predetermined magnitude; and discriminating between those groups of saccadic movements which include said second saccade and those which do not.

7. A method as defined in claim 6 further comprising:

detecting within a first segment of each of said portions of said extended time interval, the existence of double eye movements having a short duration characteristic of a blink; and discriminating between said saccadic movements and said blink movements.

8. An apparatus for objectively testing the visual field of a subject comprising:

means for presenting a reference fixation target within the subject's visual field;

means for presenting a target image to the subject at a selected location within the subject's visual field at a selected angular distance from said reference target and for a predetermined time interval;

means for monitoring the position and movement of the subject's eye at least during an extended time interval which includes and which extends beyond said predetermined time interval, said monitoring means being constructed and arranged to provide an electrical output signal of an amplitude corresponding to the magnitude of movement of the subject's eye; and circuit means having an input connected to the output of said monitoring means and having an input from said target image presentation means for determining whether the subject actually visually detected a presented target image by electronically detecting the number and magnitude of the subject's eye movements during said extended time interval.

9. An apparatus as defined in claim 8 wherein said circuit means comprises, at least in part:

means for detecting, within said extended time interval, groups of at least three output signals from said monitoring means and in which the amplitude of an intermediate of said signals is more than a predetermined amount.

10. An apparatus as defined in claim 9 wherein said predetermined amplitude corresponds to a subject's eye movement of approximately 3°.

11. An apparatus as defined in claim 8 wherein said circuit means comprises, at least in part:

means for detecting, within said extended time interval, groups of at least three output signals from said monitoring means and in which the amplitude of the first of said signals corresponds to an eye movement which does not differ from said selected angular distance by more than a predetermined amount and in which the amplitude of the succeeding of said signals is no greater than that which would correspond to an eye movement which is no more than said predetermined amount.

12. An apparatus as defined in claim 8 wherein said circuit means comprises, at least in part:

means for detecting, within said extended time interval, the existence of only two output signals from said monitoring means, each of said two output signals being of an amplitude which corresponds to an eye movement of a magnitude substantially equal to said selected angular distance.

13. An apparatus as defined in claim 8 wherein said circuit means comprises:

a primary channel having an output connected to an output gate, said primary channel being constructed and arranged to apply a pulse to said output gate and in response to an input signal to said primary channel and at the end of said extended time interval;

said monitoring means including an output connected to the input to said primary channel;

said primary channel including, at its input, means for enabling only those of the output signals from said monitoring means which have an amplitude more than that which corresponds to a predetermined magnitude of eye movement to be applied to the input of said primary channel;

means for enabling said output gate, at least at the end of said extended time interval; and whereby an eye movement of a magnitude at least equal to said predetermined magnitude will switch the output of said output gate at the end of said extended time interval.

14. An apparatus as defined in claim 8 wherein said circuit means further comprises:

a primary channel having an output connected to an output gate, said primary channel being constructed and arranged to apply a pulse to said output gate in response to an input signal to said primary channel and at the end of said extended time interval;

said monitoring means including a first output connected to the input to said primary channel;

said primary channel including, at its input, means for enabling only those of the output signals from monitoring means which have an amplutude of more than that which corresponds to a predetermined magnitude of eye movement to be applied to the input to said primary channel;

a second channel having an output connected to said output gate, said second channel being constructed and arranged to disable said output gate in response to an input signal to said second channel;

said monitoring means including a second output connected to the input to said second channel;

said second channel including, at its input, means for enabling only those of the output signals from said monitoring means which have amplitude more than that which corresponds to a second predetermined magnitude of eye movement, which second predetermined magnitude is greater than said first predetermined magnitude, to be applied to the input of said second channel;

means responsive to an initial signal to said primary channel for enabling said second channel for a predetermined time interval after said first signal; and means connecting said primary and second channels for reenabling said output gate in response to a third signal applied to said primary channel within said extended time interval.

15. An apparatus as defined in claim 14 further comprising:

means for manually and independently disabling said second channel whereby said circuit means will be responsive solely to the first and said eye movements.

16. An apparatus as defined in claim 14 further comprising:

a third channel having an input connected to an output from said monitoring means, said third channel having an output connected to said primary channel for selectively enabling or disabling said primary channel;

said third channel being constructed and arranged to disable said primary channel in response to a pulse signal from said monitoring means in which said signal has a period of up to approximately 50 milliseconds and being characteristic of a blink; and said primary and second channels including means for delaying operation of said channels until after said third channel has selectively enabled or disabled said primary channel.

17. A method for determining the visual field of a subject comprises:

providing a reference fixation target within the subject's visual field;

thereafter presenting a target image to the subject at a location spaced from said reference fixation target but within his expected visual field;

electronically determining whether the subject actually visually detected said presented target image; and in response to an indication that the subject did not actually visually detect said presented target image, thereafter automatically and sequentially presenting a plurality of individual secondary target images, each of said secondary target images being presented at equally spaced locations with respect to the location of said first presented target image, and determining, by electronic detection of the eye movements of the subject, which of said secondary targets were actually seen.

18. A method as defined in claim 17 wherein said sequentially presentation of said secondary target images includes presentation of at least three such images disposed in a generally triangular pattern surrounding the location of said first presented target.

19. A method as defined in claim 18 wherein said secondary target images are each spaced approximately 1° from the location of the first presented target image.

20. An apparatus for determining the visual field of the subject comprising:

means for displaying a reference fixation target within the subject's expected visual field;

means for presenting a target image to the subject within his expected visual field and at a location spaced from that of said reference fixation target;

means for monitoring the subject's eye positions and movements;

means for detecting those of the subject's eye positions and movements which display at least one characteristic indicative of whether the subject actually visually detected said presented target image;

means responsive to detection by said detection means of the subject's having failed to visually detect an actually presented target for thereafter sequentially presenting a plurality of individual, secondary target images, each of said secondary target images being presented at equally spaced locations with respect to the location of said first presented target image; and said means for monitoring the subject's eye positions and movements including means for electronically monitoring the subject's position and eye movements for each of said presented secondary target image to determine whether said subject actually visually detected said secondary target images.

21. An apparatus as defined in claim 20 further comprising:

said means for presenting said target image including means for directing a beam of light toward a surface within the subject's expected visual field;

directional control means for varying the direction of said beam to enable a plurality of target images to be presented at various locations;

digital input information means constructed and arranged to receive digital information corresponding to selected locations of said target image and being operatively associated with said directional control means to sequentially position the direction of said beam to said selected locations;

means for monitoring the subject's eye positions and movements in response to presentation of said target images and for detecting and discriminating between those of the presented targets which the subject has actually visually detected and those which he has not;

means responsive to detection of the subject's having failed to actually visually detect a presented target for disabling said operative association between said digital input information means and said directional control means; and means for thereafter sequentially presenting a plurality of individual secondary target images at equally spaced locations with respect to the location of said target image which the subject failed to actually visually detect, and including secondary target positioning means operatively associated with said directional control means for controlling the direction of said light beam independently of said digital input information means.

22. An apparatus as defined in claim 21 further comprising:

said secondary target positioning means including means for operating said directional control means to reposition the location of said target image to the position within the subject's visual field in which said last target image was presented, after completion of the presentation of said individual secondary target images; and means for disabling said operative association between said secondary target positioning means and said directional control means and for reestablishing the operative association between said digital input information means and said directional control means.

* * * * *